US012319903B2

(12) United States Patent
Balachandran et al.

(10) Patent No.: US 12,319,903 B2
(45) Date of Patent: Jun. 3, 2025

(54) ELASTICALLY DEFORMABLE COMPONENTS AND ASSEMBLIES FOR USE IN CELLULAR ASSAYS

(71) Applicant: THE BOARD OF TRUSTEES OF THE UNIVERSITY OF ARKANSAS, Little Rock, AR (US)

(72) Inventors: Kartik Balachandran, Fayetteville, AR (US); Nasya Moriah Sturdivant, Raleigh, NC (US)

(73) Assignee: THE BOARD OF TRUSTEES OF THE UNIVERSITY OF ARKANSAS, Little Rock, AR (US)

( * ) Notice: Subject to any disclaimer, the term of this patent is extended or adjusted under 35 U.S.C. 154(b) by 682 days.

(21) Appl. No.: 17/145,030

(22) Filed: Jan. 8, 2021

(65) Prior Publication Data

US 2021/0238524 A1 Aug. 5, 2021

Related U.S. Application Data

(60) Provisional application No. 62/958,472, filed on Jan. 8, 2020.

(51) Int. Cl.
*C12M 1/00* (2006.01)
*C12M 1/42* (2006.01)
*C12N 5/071* (2010.01)
*C12N 5/079* (2010.01)

(52) U.S. Cl.
CPC ............ *C12M 23/34* (2013.01); *C12M 29/04* (2013.01); *C12M 35/08* (2013.01); *C12N 5/0622* (2013.01); *C12N 5/0697* (2013.01); *C12N 2502/08* (2013.01); *C12N 2502/28* (2013.01)

(58) Field of Classification Search
CPC ...... C12M 23/34; C12M 29/04; C12M 35/08; C12N 5/0622; C12N 5/0697; C12N 2502/08; C12N 2502/28
USPC ......................................... 435/297.1
See application file for complete search history.

(56) References Cited

U.S. PATENT DOCUMENTS 10,961,496 B2 * 3/2021 Levner ................. C12N 5/0622
2017/0370908 A1 * 12/2017 Dauth .................. C12N 5/0697

FOREIGN PATENT DOCUMENTS

CN 107312713 A * 11/2017 ............ C12M 21/08

OTHER PUBLICATIONS

Shan et al. (2015), Rigidity-tuning conductive elastomer, Smart Mater. Struct. 24 065001 (Year: 2015).*

(Continued)

*Primary Examiner* — Michael L Hobbs
*Assistant Examiner* — Lenora A Abel
(74) *Attorney, Agent, or Firm* — Quarles & Brady, LLP

(57) ABSTRACT

The present invention provides elastic assemblies used to model tissues or organs of interest. In one embodiment, detailed herein, the assemblies are designed to model the blood brain barrier following a traumatic brain injury. The present invention also provides elastic membranes on which the assemblies are built, kits from which the assemblies may be prepared, and systems that expand upon the assemblies, forming more physiologically relevant models. Methods for making and using the disclosed devices are also provided.

20 Claims, 19 Drawing Sheets

(56) References Cited

OTHER PUBLICATIONS

Park et al. (2004), Mechanical response of bovine articular cartilage under dynamic unconfined compression loading at physiological stress levels, OsteoArthritis and Cartilage (2004) 12, 65-73 (Year: 2004).*
CN-107312713A Machine English Translation (Year: 2017).*
Shan et al., Rigidity-tuning conductive elastomer, 2015, Smart Materials and Structures, 24 (Year: 2015).*
Park et al., Mechanical response of bovine articular cartilage under dynamic unconfined compression loading at physiological stress levels, 2004, OsteoArthritis and Cartilage, 12, 65-73 (Year: 2004).*
A. D. Wong, M. Ye, A. F. Levy, J. D. Rothstein, D. E. Bergles and P. C. Searson, "The blood-brain barrier: an engineering perspective," Frontiers in Neuroengineering, vol. 6, No. 7, pp. 1-22, 2013.
A. Epshteyn, S. Maher, A. Taylor, A. Holton, B. J.T. and J. Cuiffi, "Membrane-integrated microfluidic device for high-resolution live cell imaging," Biomicrofluidics, vol. 5, No. 4, 2011.
A. Marty, C. Causserand, C. Rogues and P. Bacchin, "Impact of tortuous flow on bacteria streamer development in microfluidic system during filtration," Biomicrofluidics, vol. 8, No. 1, 2014.
B. Chueh, D. Huh, C. Kyrtsos, T. Houssin, F. N. and S. Takayama, "Leakage-Free Bonding of Porous Membranes into Layered Microfluidic Array Systems," Analytical Chemistry, vol. 79, No. 9, pp. 3504-3508, 2007.
B. Obermeier, R. Daneman and R. M. Ransohoff, "Development, maintenance, and disruption of the blood-brain barrier," Nature Medicine, vol. 19, No. 12, pp. 1584-1596, 2013.
B. R. Flachsbart, K. Wong, J. M. Iannacone, E. N. Abante, R. L. Vlach, P. A. Rauchfuss, P. W. Bohn, S. J. V. and M. Shannon, "Design and fabrication of a multilayered polymer microfluidic chip with nanofluidic interconnects via adhesive contact printing," Lab on a Chip, vol. 6, No. 5, pp. 667-674, 2006.
B. V. Zlokovic, "The Blood-Brain Barrier in Health and Chronic Neurodegenerative Disorders," Neuron, vol. 57, pp. 178-201, 2008.
C. Sip and A. Folch, "Stable chemical bonding of porous membranes and poly(dimethylsiloxane) devices for long-term cell culture," Biomicrofluidics, vol. 8, No. 3, 2014.
Center for Disease Control and Prevention, "Traumatic Brain Injury and Concussion," [Online]. Available: https://www.cdc.gov/traumaticbraininjury/get_the_facts.html. [Accessed Apr. 22, 2022].
D. Huh, H. Kim, J. Fraser, D. Shea, K. Mohammed, A. Bahinski, G. Hamilton and D. Ingber, "Microfabrication of human organs-on-chips," Nature Protocols, vol. 8, No. 11, pp. 2135-2157, 2013.
D. R. Namjoshi, C. Good, W. H. Cheng, W. Panenka, C. P. A. D. Richards and C. Wllington, "Towards clinical management of traumatic brain injury: a review of models and mechanisms from a biomechanical perspective," Disease Models & Mechanisms, pp. 1325-2338, 2013.
E. Vandenhaute, A. Drolez, E. Sevin, F. Gosselet, C. Mysiorek and M. Dehouck, "Adapting coculture in vitro models of the blood-brain barrier for use in cancer research: maintaining an appropriate endothelial monolayer for the assessment of transendothelial migration," Laboratory Investigation, vol. 96, pp. 588-598, 2016.
I. Humphreys, R. L. Wood, C. J. Phillips and S. Macey, "The costs of traumatic brain injury: a literature review," Clinicoeconomics and Outcomes Research, vol. 5, pp. 281-287, 2013.
J. Kawada, H. Kimura, H. Akutsu, Y. Sakai and T. Fujii, "Spatiotemporally controlled delivery of soluble factors for stem cell differentiation," Lab on a Chip, vol. 12, No. 21, pp. 4508-4515, 2012.
K. Aran, L. Sasso, N. Kamdar and J. Zahn, "Irreversible, direct bonding of nanoporous polymer membranes to PDMS or glass microdevices," Lab on a Chip, vol. 10, No. 5, pp. 548-555, 2010.
K. Jiao, C. Graham, J. Wolff and P. Kohli, "Modulating molecular and nanoparticle transport in flexible polydimethylsiloxane membranes," Journal of Membrane Science, vols. 401-402, pp. 25-32, 2012.
K. McCarthy and J. de Vellis, "Preparation of Separate Astroglial and Oligodendroglial Cell Cultures from Rat Cerebral Tissue," The Journal of Cell Biology, vol. 85, No. 3, pp. 890-902, 1980.
L. Cucullo, N. Marchi, M. Hossain and J. D., "A Dynamic in vitro BBB Model for the Study of Immune Cell Trafficking into the Central Nervous System," Journal of Cerebral Blood Flow & Metabolism, vol. 31, No. 2, 2010.
L. Xiao-Dong, Y. Zhi-Hong and Y. Hiu-Wen, "Repetitive/temporal hypoxia increased P-glycoprotein expression in cultured rat brain microvascular endothelial cells in vitro," Neuroscience Letters, vol. 432, No. 3, pp. 184-187, 2008.
L. Yang, K. Shah and Abbruscato, "An In Vitro Model of Ischemic Stroke,," Astrocytes, vol. 214, pp. 451-466, 2011.
M. Blanchette and R. Daneman, "Formation and maintenance of the BBB," Mechanisms of Development, vol. 138, pp. 8-16, 2015.
M. van der Helm, A. van der Meer, J. Eijkel, A. van der Berg and L. Segerink, "Microfluidic organ-on-chip technology for blood-brain barrier research," Tissue Barriers, vol. 4, No. 1, 2016.
N. J. Abbott, L. Ronnback and E. Hansson, "Astrocyte-endothelial interactions at the blood-brain barrier," Nature Reviews Neuroscience, vol. 7, pp. 41-53, 2006.
Neal, Emma H., et al. "A simplified, fully defined differentiation scheme for producing blood-brain barrier endothelial cells from human iPSCs." Stem cell reports 12.6 (2019): 1380-1388.
T. Scharnweber, R. Truckenmuller, A. Schneider, A. Welle, M. Reinhardt and S. Giselbrecht, "Rapid prototyping of microstructures in polydimethylsiloxane (PDMS) by direct UV-lithography," Lab on a Chip, vol. 11, No. 7, pp. 1368-1371, 2011.

* cited by examiner

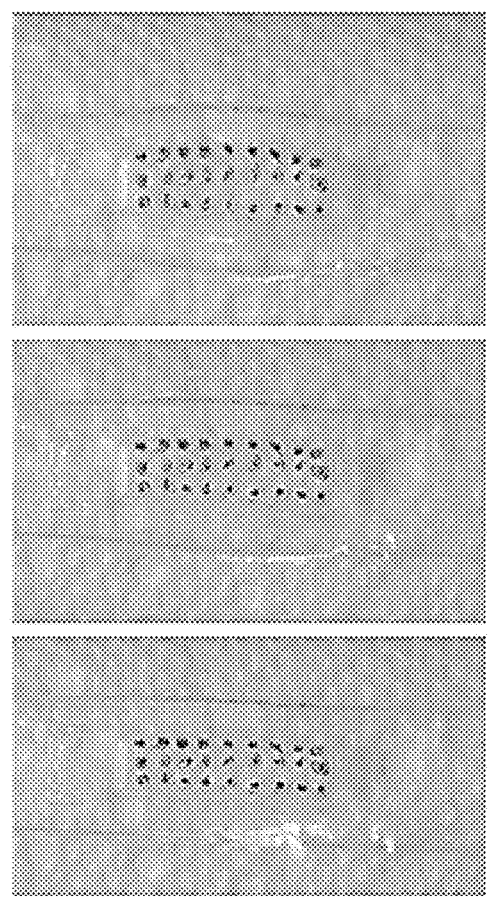
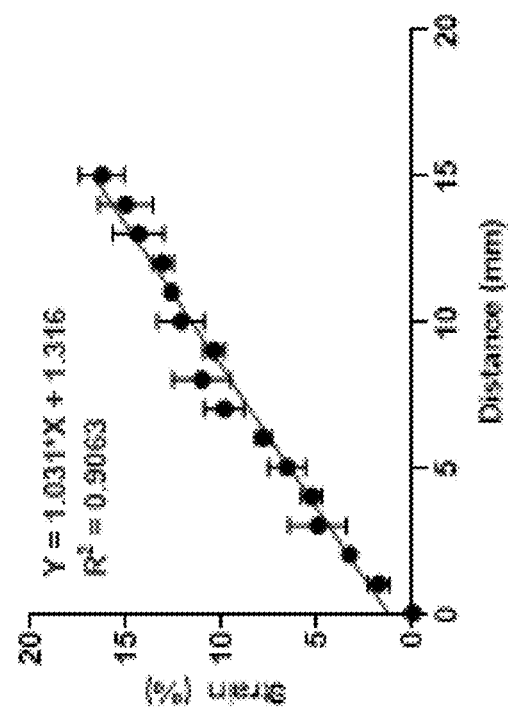
FIG. 16A
FIG. 16B

ELASTICALLY DEFORMABLE COMPONENTS AND ASSEMBLIES FOR USE IN CELLULAR ASSAYS

CROSS-REFERENCE TO RELATED APPLICATIONS

This application claims benefit of priority to U.S. Provisional Patent Application No. 62/958,472, filed Jan. 8, 2020, the contents of which is incorporated by reference in its entirety.

STATEMENT REGARDING FEDERALLY SPONSORED RESEARCH

This invention was made with government support under grant numbers 1452943 and 1761071 awarded by National Science Foundation. The government has certain rights in the invention.

BACKGROUND

A traumatic brain injury (TBI) is an extreme insult to the head initiated by an external mechanical force, such as a blow or a jolt, resulting in damage to the brain [1, 2]. Since the early 2000s, TBI's have become more prevalent and publicized due to the number of battlefield injuries in the Afghanistan and Iraq War and the increasing number of diagnosed TBI's in contact sports. In the United States, there are an estimated 1.7 million new cases of TBI each year [1]. Worldwide, an estimated 10 million people will be affected by a TBI annually [3]. Other common causes of a TBI include falls, motor vehicle accidents, assaults, and being struck by or against and object. Following TBI, the BBB is disrupted allowing for plasma components, red blood cells, and leukocytes to leak into the brain compromising synaptic and neuronal functions [4]. The blood-brain barrier (BBB) is a network of capillaries, which takes up approximately 20 $m^2$ per 1.3 kg of brain [5] and controls the passage of ions and molecules from the blood to the brain. The cerebral vasculature has two key functions: to deliver the necessary nutrients to maintain a high-functioning and metabolically active brain and to protect the brain from harmful substances circulating in the bloodstream [5, 6]. With the increasing amount of research implicating BBB disruption in neurodegenerative diseases, such as Parkinson's and Alzheimer's disease, there is a need to make more physiologically relevant BBB models that can reproduce the mechanisms by which damage to the BBB occurs.

Several BBB-on-chip configurations have been designed and engineered to include physiologically relevant components, such as glial cells, fluid flow (mimetic of blood flow), and three-dimensional brain environments. To date, ten publications describe BBB-on-chips that have been developed to model the anatomical, physiological, and dynamic nature of the BBB [7]. These models have been used to study drug delivery, cancer cell migration through the BBB [8], ischemic stroke [9], immune cell trafficking into the central nervous system [10], hypoxia [11], and many other diseases that affect the brain. However, six of the ten published BBB-on-chips have a glass layer and the remaining four utilize an inelastic membrane, making them incapable of enduring a mechanical insult memetic of a TBI [7]. Thus, there remains an urgent need in the art for dynamic benchtop platforms to investigate the effect of a TBI on the blood brain barrier.

SUMMARY

Disclosed herein are elastically deformable components, assemblies, systems, and kits for use in cellular assays including methods of making and using the same. One aspect of the technology provides for elastic assemblies for use in a cellular assay and components thereof. The elastic assembly may comprise a luminal compartment, the luminal compartment having a media inlet and media outlet and configured to house a first cell and have a media flow therethrough; an abluminal compartment configured to house a second cell; an elastic membrane, the elastic membrane comprising a plurality of pores therethrough and configured to separate the luminal compartment from the abluminal compartment; and an anchoring membrane mechanically coupled to each of the elastic membrane, the luminal compartment, and the abluminal compartment where each of elastic membrane, the first compartment, and the second compartment are capable of elastic deformation when the physiological stress is applied to the anchoring member. In some embodiments, the luminal compartment, the abluminal compartment, the elastic membrane comprise, or any combination thereof comprise an elastomer, such as a polysiloxane, e.g., PDMS. In some embodiments, the components of the assembly or the elastomer has an elastic modulus of 1 kPa-5 MPa.

Another aspect of the technology provides for a system for use in a cellular assay. The system may comprise any of the assemblies or assembly components described herein and further comprise one or more of an actuator mechanically coupled to the anchoring member, a pump in fluid communication with the luminal compartment and configured to pump a media through the luminal compartment, a detection system, or any combination thereof. In some embodiments, the system comprises each of the actuator, the pump, and the detection system.

Another aspect of the technology provides for kits for preparing any of the assemblies described herein. In some embodiments, the kit comprises one or more of the elastic membrane, the luminal compartment, the abluminal compartment, the anchoring member, the first cell, the second cell, the extracellular matrix hydrogel, the extracellular protein, the media, a sealant, or any combination thereof. In some embodiments, the kit comprises each of the elastic membrane, the luminal compartment, the abluminal compartment, the anchoring member and, optionally, one or more of the extracellular matrix hydrogel, the extracellular protein, the media, or the sealant.

Another aspect of the invention provides for method for performing a cellular assay. The method may comprise providing any of the assemblies or systems described herein seeded with a first cell and a second cell and detecting a characteristic of the first cell seeded into assembly, the second cell seeded into the assembly, or both. In some embodiments, the method further comprises comprising applying a stimulus to the assembly. The stimulus may be applied before or after the detection step. In certain embodiments, the characteristic is detected both before and after the stimulus is applied. In some embodiments, the stimulus is a mechanical stimulus, an electrical stimulus, a chemical stimulus, or any combination thereof. In some embodiments, the stimulus may be an acute stress or a repetitive stress of 1 kPa-5 MPa. In some embodiments, the stimulus is an associated with a physiological stress, including without limitation a physiological stress is associated with traumatic brain injury (TBI), a beating heart, blood flow, or hypertension.

Methods of preparing an assembly for use in a cellular assay are also provided for. The method may comprise seeding a luminal compartment with a first cell, seeding an abluminal compartment with a second cell, and coupling each of the luminal compartment and the abluminal compartment to an elastic membrane, the membrane comprising a plurality of pores therethrough mechanically coupled to an anchoring member where each of the first compartment, the second compartment, and the membrane are capable of elastic deformation when a physiological stress is applied to the anchoring member. In some embodiments, the method may further comprise coupling an actuator to the anchoring member, fluidly coupling a pump with the luminal compartment, integrating a detection system with the assembly, or any combination thereof.

These and other aspects of the invention will be further described herein.

BRIEF DESCRIPTION OF THE DRAWINGS

FIG. 10A shows a scanning electron microscope image, and FIG. 10B shows a multiphoton image. In both images, black circles represent areas where there is no PDMS present (i.e., the pores).

FIG. 13A shows the percent stretch and FIG. 13B shows the stretch duration.

FIG. 16A-16F shows the tissue-chip platform used for oscillatory flow simulations. FIG. 16A shows the cell compartment being stretched. Fiducial markings used to demonstrate the stretch of the porous membrane. FIG. 16B shows strain-distance plot showing the uniformity of strain on the porous membrane. FIG. 16C shows oscillatory flow waveform imposed in chip flow channels. (FIG. 16D) Velocity magnitude, (FIG. 16E) velocity profile, and (FIG. 16F) Shear stress profile data from three representative time snapshots indicated by the asterisks in panel (FIG. 16C) are shown.

(FIG. 17B) GLUT1; and (FIG. 17C) occludin expression in differentiated BMECs.

DETAILED DESCRIPTION

Disclosed herein are elastically deformable components, assemblies, systems, and kits for use in cellular assays including methods of making and using the same. The present technology allows cells to be subjected to mechanical stimuli or stresses. To accommodate these stresses, the devices of the present invention are designed to be elastically deformable.

Assemblies

Figure 1:
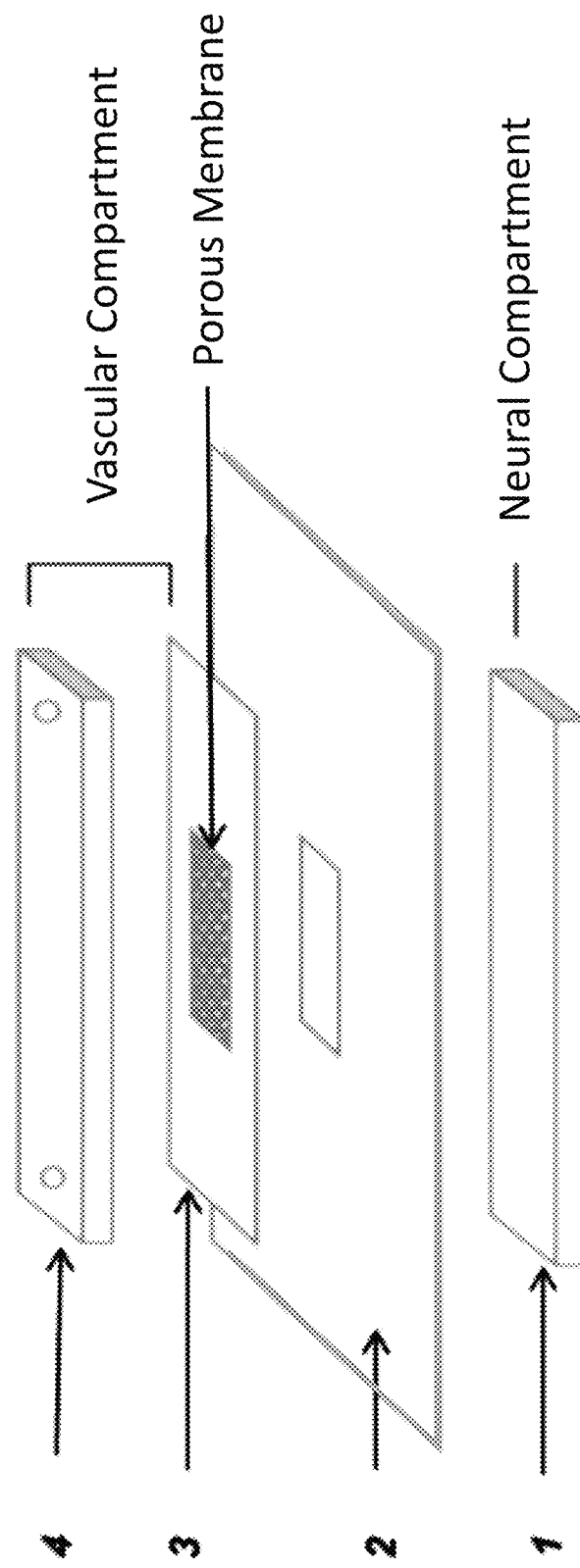
FIG. 1 shows a schematic of the construction of one embodiment of the BBB-on-Chip.

The present invention provides for elastic assemblies for use in a cellular assay. FIG. 1 illustrates an elastic assembly comprising a porous elastic membrane 3, a luminal compartment having a media inlet and media outlet configured for housing a first cell and to have media flow therethrough 4, a subluminal compartment for housing a second cell 1, and an anchoring member 2. In some contexts, the luminal compartment 4 and the subluminal compartment 1 may be referred to as a vascular compartment and neural compartment, respectively. To form the assembly, each of the luminal compartment 4, porous elastic membrane 3, and the subluminal compartment 1 are mechanically coupled to the anchoring member 2. Each compartment and membrane must be capable of elastic deformation when the physiological stress is applied to the anchoring member. In some embodiments, the luminal compartment 4 is seeded with a first cell and/or the subluminal compartment 1 is seeded with a second cell.

The seeded cells may be chosen to mimic a bodily tissue. For illustration, the assembly described in the Examples, which may be referred to as a "BBB-on-Chip", was designed to model the blood-brain barrier (BBB). The term "BBB-on-Chip" is used to describe a small, dynamic benchtop model of a component of the BBB. Suitably, the model may be of the neurovascular unit. As described and illustrated below the BBB-on-Chip is mechanotransductive and able to be used to study the blood-brain barrier (BBB) following a traumatic brain injury (TBI).

Figure 2:
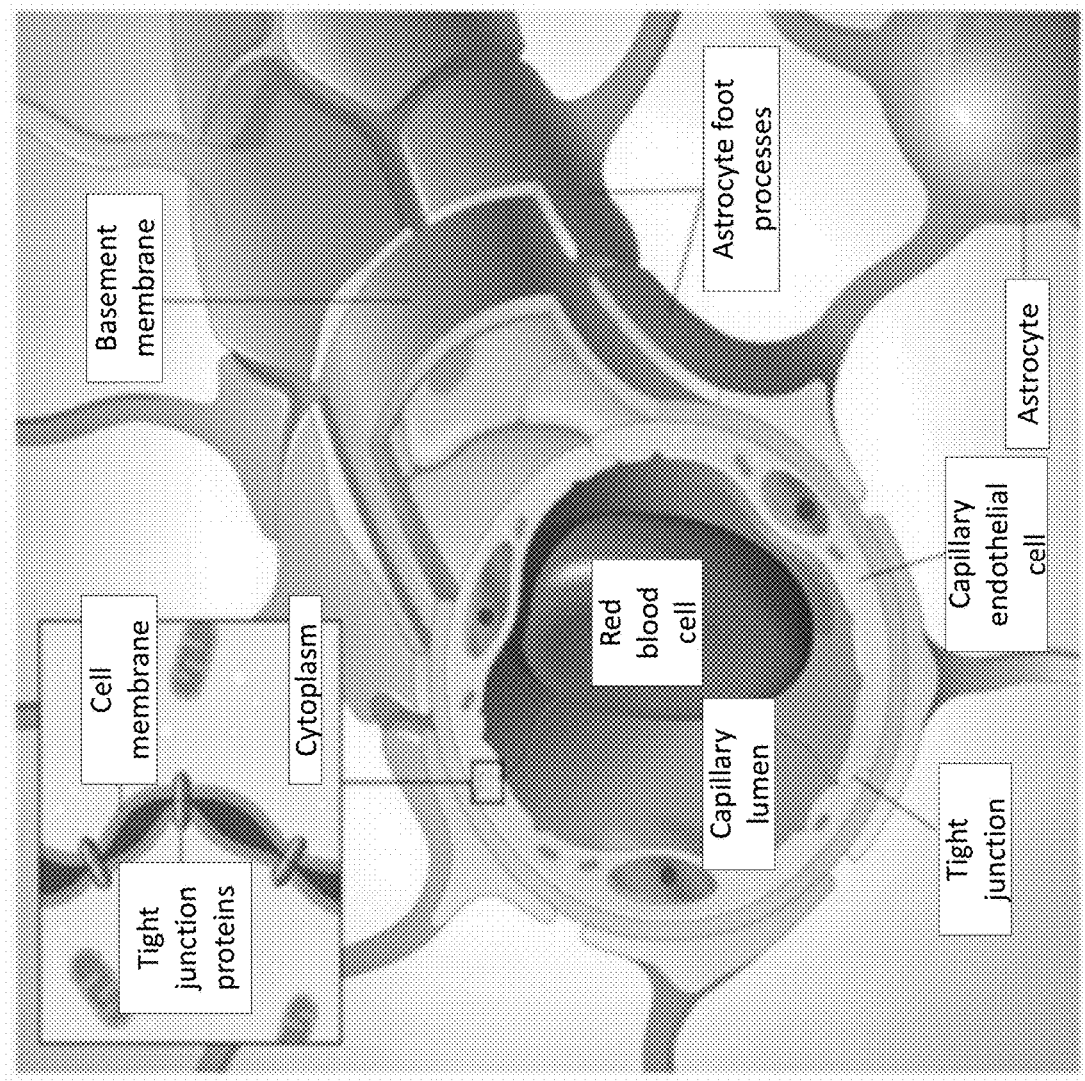
FIG. 2 shows a schematic of the blood-brain barrier (BBB).

As illustrated in FIG. 2, the BBB is comprised of brain microvascular endothelial cells (also referred to herein as microvascular endothelial cells or MVECs). These cells lack fenestrations and form extensive tight junctions with neighboring cells. As a result, both paracellular and transcellular movement of molecules is significantly limited across the BBB, as compared to barriers formed by vascular endothelial cells in the rest of the body. In addition to MVECs, astrocytes are the second primary cell type required to reproduce the BBB in vitro. Astrocyte end-feet ensheath blood vessels within the BBB and contribute to increased tight junction expression, increased trans-endothelial electrical resistance (TEER), upregulated expression and polarized localization of transporters, and increased specialized enzyme systems [12, 5, 6, 13].

Figure 3:
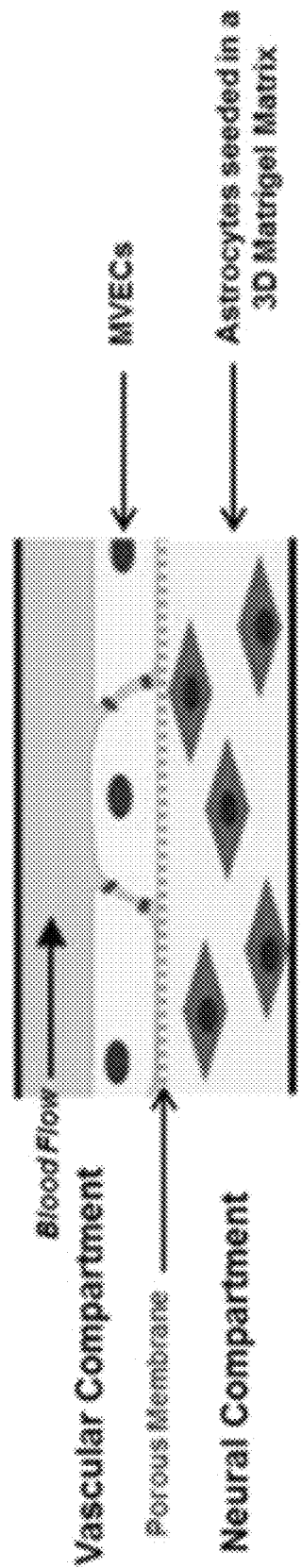
FIG. 3 shows a schematic of one embodiment of the BBB-on-Chip.

In some embodiments the first and second cells are selected from vascular and/or neural cells present at the BBB. Accordingly, both compartments may house cells of these types or different cell types to model a particular bodily tissue separated by the elastic membrane. For example, the assembly may comprise a luminal compartment for housing MVECs or other vascular cell types (i.e., a vascular compartment) and subluminal compartment for housing astrocytes or other neural cell types (i.e., a neural compartment) as to mimic the microenvironment of the BBB (FIG. 3). As illustrated in FIG. 3, the assembly may be configured to allow for media, such as blood, to flow through the luminal (i.e., vascular) compartment to mimic the BBB.

The assemblies of the present invention are not limited to those that model the BBB. The assemblies may be configured to model any tissue or organ of interest. Suitable tissues and organs include, without limitation, a lung, a liver, a kidney, skin, an eye, a brain, a blood-brain-barrier, a heart, a heart valve, vasculature, a gastrointestinal tract, airways, a reproductive organ, a tumor, bladder, skeletal muscle, or a combination of two or more thereof. In some embodiments, the assemblies are seeded with cells associated with the brain microenvironment, such as microvascular endothelial cells (MVECs), astrocytes, pericytes, oligodendrocytes, microglia, and neurons. In other embodiments, the assemblies are seed with cells associated with endothelial or epithelial tissues. Exemplary assemblies may include heart valveendothelial cells in a luminal compartment and heat valve interstitial cells in an abluminal compartment or nasal epithelial cells in a luminal compartment and capillary microvascular endothelial cells in an abluminal compartment. However, any cell type may be used with the present invention. Advantageously, the cell type is selected to model the tissue or organ of interest. Further, in some embodiments, multiple cells types will be combined in a single compartment. For instance, astrocytes, neurons, and pericytes may all be included in a single compartment to produce a more physiologically relevant brain model. The cells used with the present invention may be from any source, including from a commercial supplier, a cell bank, or a subject. Those of skill in the art will realize that the assemblies described herein can be adapted to mimic the function of any portion of a tissue or organ in any living organism. Thus, suitable subjects include, without limitation, vertebrates (e.g., humans, fish, birds, reptiles, and amphibians), invertebrates (e.g., protozoa, annelids, mollusks, crustaceans, arachnids, echinoderms and insects), plants, fungi (e.g., mushrooms, mold, and yeast), and microorganisms (e.g., bacteria and viruses).

Any media may be used with the present invention. However, one of skill in the art will recognize that the media should be selected as to accommodate the growth and/or sustenance of the particular cell type being cultured. For instance, in the Examples, the MVECs were cultured in Endothelial Cell Medium-rat (ECM-r, ScienCell) while the astrocytes were cultured in Matrigel® Matrix (Corning, Corning, NY) rehydrated with astrocyte conditioned media. Advantageously, the media may be chosen or modified as to mimic a bodily fluid (e.g., blood, urine, saliva, mucus, tears, lymph, and interstitial fluid) associated with the in vivo environment being modeled.

Advantageously, the physiological stress applied to an assembly is representative of a stress that the modeled tissue might undergo, as to model in vivo conditions. For instance, in the Examples, the inventors subject an assembly designed to model the BBB to a stretch with a TBI-like magnitude and rate. In some embodiments, the physiological stress is an acute stress, i.e., a stress that is singular and, optionally, severe. In other embodiments, the stress is repetitive. Optionally, the stress may mimic a stress associated with traumatic brain injury. Suitable stresses include, without limitation, tensile (e.g., uniaxial, biaxial, or equiaxial), compressive, torsional, and shear stresses.

One aspect of the invention provides for a porous, elastic membrane for separating cells. As used herein, the term "membrane" is used to describe a selective barrier. A selective may allow some molecules, ions, or other particles to pass but stops others or allow some molecules, ions, or other particles to pass but prevent cells from migrating from one compartment to another. Within the assembly, the membrane serves as a barrier between two cellular compartments, permitting the device to be three-dimensional and multilayered. As a result, the assemblies provided herein are more representative of the in vivo structure of the BBB as compared to a two-dimensional model (e.g., transwell plates). As shown in the Examples, the inventors describe a chip in which the membrane facilitates an organized co-culture of microvascular endothelial cells (MVECs) and astrocytes, while still permitting crosstalk between the separated cells. Accordingly, in some embodiments, the membrane has a thickness of no greater than 20 µm, 15 µm, or 10 µm.

The membranes of the present invention comprise a plurality of pores therethrough. As used herein, the term "pore" is used to describe a small hole in the membrane through which gases, liquids, and small particles can pass, but small enough cells do not pass through. The elastic membranes provided herein are largely defined by the size and spacing of their pores. In some embodiments, the pores have an inter-pore spacing of less than 30 µm and/or each pore has a diameter less than 10 µm. Suitably, the inter-pore spacing may be less than 25 µm, 20 µm, or 15 µm and/or each pore has a diameter less than 9 µm, 8 µm, 7 µm, 6 µm, 5 µm, 4 µm, 3 µm, or 2 µm.

The membranes provided herein are mechanically coupled to an anchoring member, such that the membrane is capable of elastic deformation when a physiological stress is applied to the anchoring member. As used herein, the term "mechanically coupled" is used to describe components that are connected such that a mechanical force applied to one of the components is experienced, at least in part, by the other component. The anchoring member provides a surface to which a physiological stress may be applied to the membrane and/or the entire assembly. In some embodiments, the anchoring member 2 is a sheet of elastomeric material that borders the membrane 3 (FIG. 3). In the Examples, the assembly is stretched by bracing the anchoring member within metal clamps attached to a high-speed stretching device.

As used herein, the term "elastic deformation" or "elastically deformable" is used to describe a temporary shape change in response to a force that is completely or substantially self-reversing after the force is removed. All the structural components of the assembly provided herein, including the membrane, must be capable of elastic deformation, such that the integrity of these components is largely intact after the force is removed. This property ensures that the cellular changes that are detected by assay are a result of a cellular response to the physiological stress and not a response to assembly destruction. To this end, both the membrane, the anchoring member, and all other components of the assembly (see below) may be composed of an elastomer. As used herein, the term "elastomer" refers to a polymer with elastic properties.

Most microfluidic devices rely on commercially available polycarbonate (PC) and polyethylene terephthalate (PET) membranes. These membranes offer the advantage of sub-micron pore sizes. However, they come with several disadvantages, including poor adhesion to fluidic channels and limited translucency. Critically, their use in a dynamic model of the BBB is limited by their brittleness and high elastic modulus (~GPa). The term "elastic modulus" refers to a quantity that measures a substance's resistance to being deformed elastically (i.e., non-permanently) when a stress is applied to it. The membranes used with the present invention have an elastic modulus in the kPa to MPa range, as to model a soft biological tissue. Suitably the membranes have an elastic modulus from 1 kPa to 5 MP. PC and PET membranes may be sandwiched between a layers using standard adhesives [14], polydimethysiloxane gluing [15], $SiO_2$ sputtering [16], and silane coupling [15]. However, such systems often experience leaks, and adhesive or coupling agents can result in contamination of the high-resolution structures [17, 18, 19]. Thus, the elastic membranes disclosed herein offer a substantial advantage over the prior art.

In some embodiments, the membranes of the present invention are composed of a polysiloxane, i.e., a silicone polymer. In the Examples, the inventors fabricated membranes composed of polydimethysiloxane (PDMS), which were prepared using the methods disclosed below. PDMS is a silicone elastomer where the elastic modulus may be tailored over a range from 1.0 kPa-5.0 MPa, 0.1-4.0 MPa or 0.5-3.0 MPa depending on the extent of crosslinking present in the PDMS [20]. Thus, inclusion of this membrane allows the assemblies of the present invention to be entirely elastic and deformable. PDMS may be reversibly or irreversibly bonded to silicon, glass, or PDMS, as to avoid system leakage, and it may be coated with parylene or other polymers to increase its inertness. Additionally, PDMS is optically transparent, making it useful for applications involving optical microscopy. For instance, this transparency allows the shape and alignment of cells housed within the chip to be assessed using an upright or inverted brightfield microscope, and for tight junctions to be observed using fluorescent microscopy. Further, PDMS is biocompatible, gas permeable, and its fabricated pores allow for crosstalk between the cells housed on either side of the membrane. In embodiments in which the assembly is designed to model a BBB, the porous nature of the membrane makes it possible to assess the permeability of the barrier (i.e., the ease of molecule passage across the barrier) and to determine how physiological stress affects its permeability. The PDMS surface can also be modified for improved cell culture. For example, PDMS can be plasma-treated, coated with proteins, such as a collagen or a fibronectin, or chemically modified via surface silanization.

The media inlet and outlet may comprise any opening that allows the compartment to be connected to a fluid flow system. The orientation of the inlet and outlet may be configured to allow for more uniform flow and/or minimize stagnation within the luminal compartment. Although FIG. 1 illustrates an inlet and outlet port in the luminal compartment 4 that is perpendicular to the direction of flow, the inlet and/or outlet ports may be aligned with or at an angle between 0° and 90° to the direction of flow. In some embodiments, the inlet and outlet may be attached to a pump system that is used to create a fluid shear flow across the cells in the luminal compartment (FIG. 4), mimicking blood flow through the capillary vasculature and allowing one to investigate the effects of varying degrees of shear stress on BBB integrity.

The assemblies may additionally comprise an extracellular matrix (ECM) hydrogel and/or extracellular matrix protein in one or both of the luminal 4 or subluminal compartments 1. ECM hydrogels are cross-linked insoluble, hydrophilic networks of polymers that at least partially resemble the physical characteristics of native ECM. These hydrogels are derived from components of the ECM (e.g., collagen, hyaluronic acid, and elastin) or complex mixtures of ECM components. In the Examples, the neural compartment is filled with Matrigel® Matrix (Corning, Corning, NY), which contains the proteins present in neurovascular basement membrane within the BBB. These proteins include collagens, laminins, and heparin sulfate proteoglycans, which are needed for astrocyte and MVEC attachment, growth, and viability. Additionally, Matrigel® provides a 3D structure for cells to grow in and separates the MVECs and the astrocyte endfeet, making the device a more physiologically relevant brain model. Importantly, Matrigel® maintains its structural integrity during and after a high-speed mechanical stretch. Further, Matrigel® offers several convenient features for cellular assessment: it is conducive to calcium signaling measurement using the Fluo-3 dye, is amenable to cell/protein extraction for gene expression studies, and Phenol-red-free Matrigel® is highly conducive for brightfield and fluorescent microscopy. However, any other ECM hydrogel may be used with the present invention and additional proteins may be added to the hydrogel, as needed by the user. For example, Matrigel® can be combined with other hydrogels and proteins, such as alginate, collagen, and/or fibronectin, to reduce costs and/or better mimic the mechanical strength of the tissue of choice.

Figure 5:
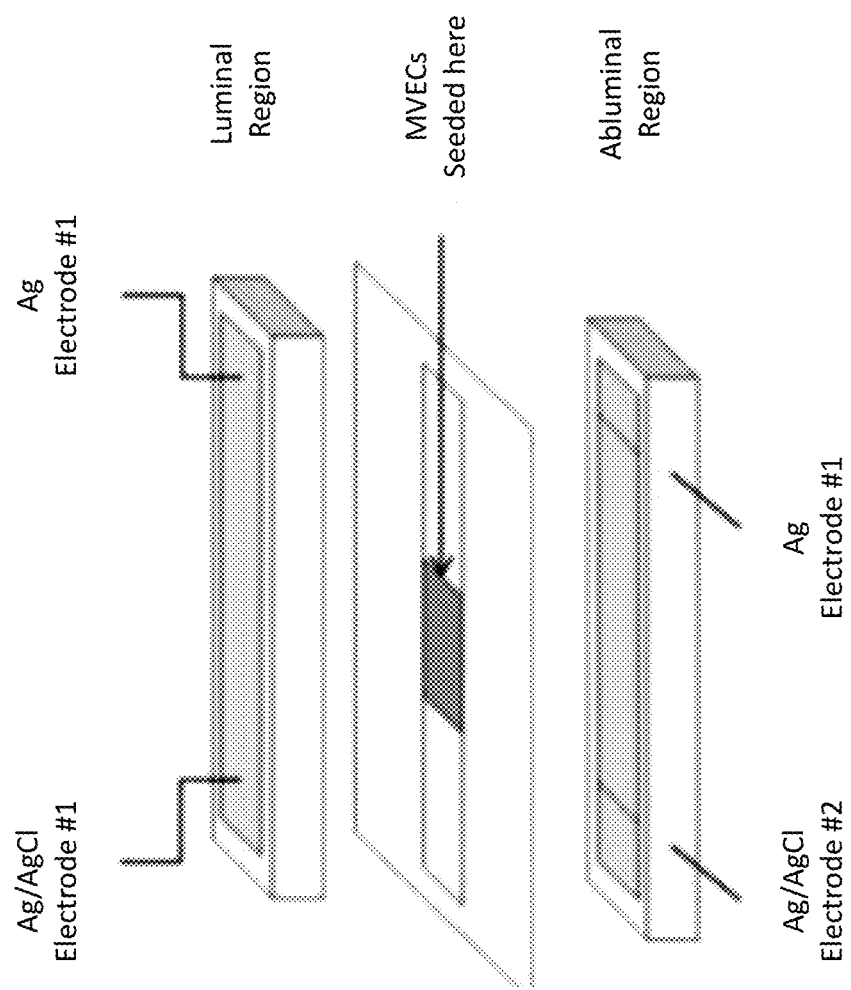
FIG. 5 shows a schematic of the TEER electrode placement within the BBB-on-Chip.

The assemblies of the present invention may be manufactured in layers, such as shown in FIG. 1. In one embodiment (described in the Examples), the assembly comprises four layers, all fabricated from transparent elastomeric polymers. Starting from the bottom of the assembly, the abluminal compartment 1 can be left cell-free, optionally comprising culture media, loaded with a monolayer of astrocytes, or loaded with a suspension of astrocytes and Matrigel®. The anchoring member 2 is an elastomer sheet with a window cut in the middle. The anchoring member 2 serves as a support layer to which the physiological stress is applied. In the Examples, anchoring member is braced between metal clamps and mounted onto a high-speed stretching device in order to stretch the entire BBB-on-Chip, transferring the mechanical deformation to the attached cells. The elastic membrane 3 may be a thin, framed, porous elastic membrane in which the inner window is capable of acting as the culture surface for cells, such as MVECs. This porous membrane partitions the luminal (or vascular) and abluminal (or neural) sides of the device and is one of the innovative aspects of this device. The fourth and final layer is a luminal (or vascular) compartment within which a fluidic channel encloses cells, such as MVECs, and contains fluid inlet and outlet ports for culture medium exchange and fluid flow. The resulting fluid shear stress on the MVEC monolayer serves to mimic blood flow. As illustrated in FIG. 5, electrodes may also be incorporated into the luminal (vascular) and abluminal (neural) sides of the device to measure trans-endothelial electric resistance (TEER). Importantly, the above description is included for illustration purposes only, as the claimed assemblies are not limited to this particular four-layer construction. For instance, the anchoring member 2 and elastic membrane 3 described above may be included as a single layer with a porous central region. Further, assemblies configured to model other tissues are considered within the scope of the present invention. For example, the assemblies may comprise more than two cellular compartments as to mimic the particular microenvironment of interest.

The cellular compartments (i.e., the luminal compartment and the abluminal compartment) may also be varied to suit the tissue being modeled and the needs of the user. For instance, in one embodiment the assembly includes an open-base neural compartment, allowing for easy access to the bottom of the membrane for the seeding and assessment of the astrocytes. In other embodiments, the device includes a closed-base neural compartment, allowing TEER measurements to be performed across the membrane via the insertion of electrodes. Further, it is not intended that the present invention be limited to a specific compartment size. In one embodiment of the chip, the vascular compartment's dimensions are 5 mm wide×2 mm high×5 cm long with inlet and outlet ports ⅛ inches in diameter, while the neural compartment's dimensions are 5 mm wide×2 mm high×5 cm long. However, the size of the compartments should be adjusted to suit both the physiological system to be modeled and the available equipment.

The chips are designed to be subjected to a physiological stress. As used herein, the term "physiological stress" is used to describe a stress characteristic of the type and magnitude that may be imposed on a bodily tissue. The physiological stress may be acute or repetitive. Exemplary physiological stresses include, without limitation, mechanical insults, tension, or stretch of tissue. For instance, the chips disclosed in the Examples were fabricated to withstand varying degrees (mild, moderate, and severe) of a stretch-induced injury. Suitably, the physiological stress is between 1 kPa-5 MPa. However, any physiological stress may be applied to the components and assemblies disclosed herein.

When the head hits an object, it results in intense mechanical loading to the brain, causing pressure gradients and tissue deformation [1]. Thus, in the Examples, the bulk structure of the BBB-on-Chip were fabricated from elastomeric materials that deform dynamically when subjected to substantial high-speed stretch, as to mimic high-speed TBIs.

Systems

The present invention also provides systems for use in a cellular assay. The systems comprise the assemblies provided herein and further comprise one of more of the following: (a) an actuator mechanically coupled to the anchoring member, (b) a pump in fluid communication with the first compartment, (c) a detection system, or (d) any combination thereof.

In embodiments in which the system comprises an actuator, the actuator is configured to apply the physiological stress to the anchoring member. As used herein, the term "actuator" refers to a moving component of a machine. The actuator used with the present invention may be configured to deliver any suitable physiological stress, including, without limitation, a mechanical insult, tension, or stretch of tissue.

Figure 4:
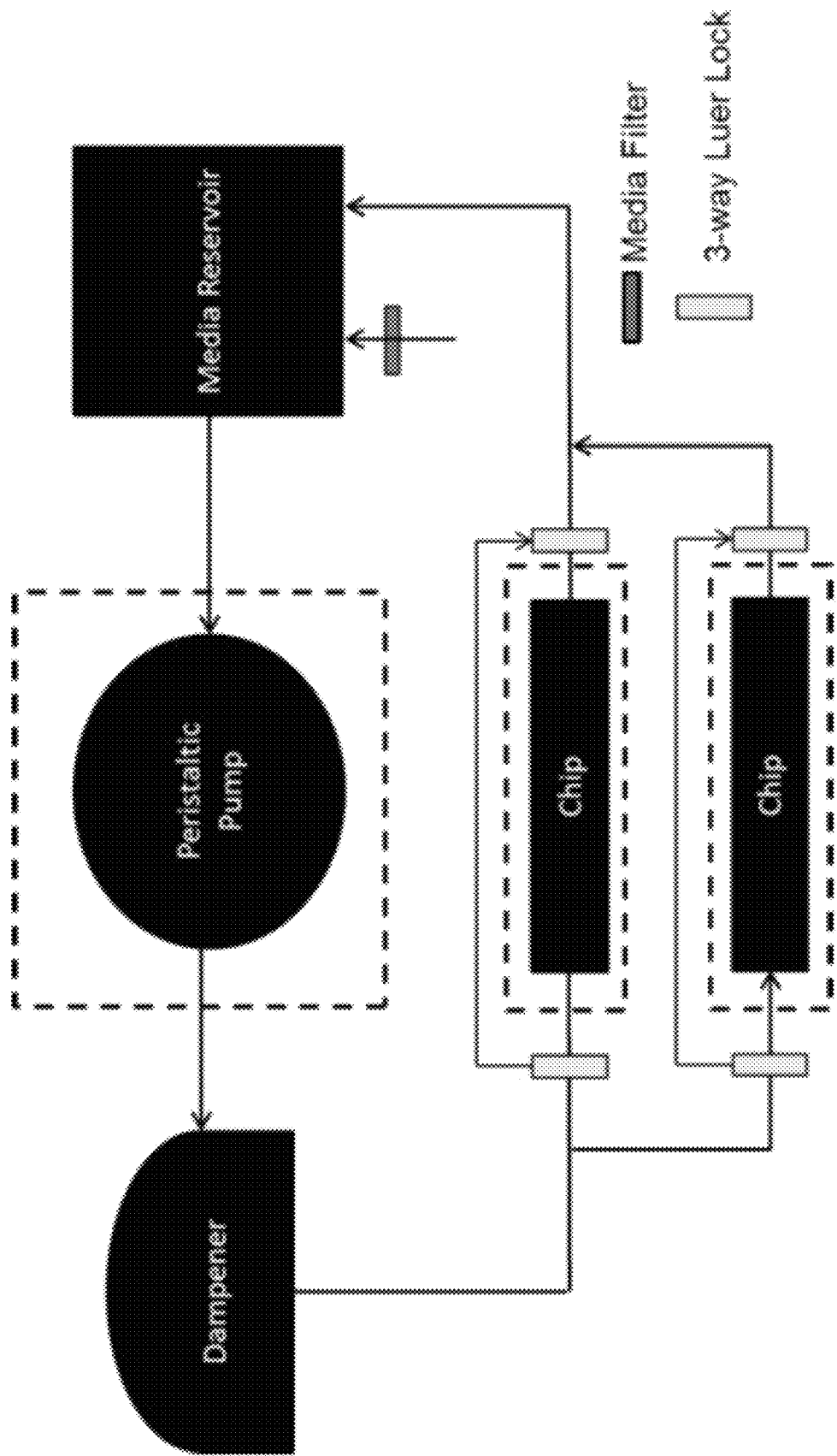
FIG. 4 shows a schematic of a fluid flow system attached to the BBB-on-Chip.

In embodiments in which the system comprises a pump, the pump is configured to circulate media through the first compartment. This may be accomplished by attaching a fluid flow system to the media inlet and media outlet of the first compartment (FIG. 4).

In embodiments in which the system comprises a detection system, the detection system may be an electrical detection system or an optical detection system. As used herein, the term "detection system" refers to any system by which a characteristic of the cells housed in the assembly may be assayed. For instance, a suitable electrical detection system may include electrodes by which voltage and current may be measured across the assembly. In the Examples, electrodes are inserted into the assembly to monitor barrier function (i.e., the permeability of the model BBB) via measurement of trans-endothelial electrical resistance (TEER). Electrodes may be integrated in a variety of configurations. For example, the inlet and outlet ports in the first compartment may be modified such that the flow tubing may be removed and replaced with a cap comprising electrodes. The electrode system may also be modified such that the assembly can be used to test the ability of electroporation to permeabilize the BBB. Alternatively, the detection system may be an optical detection system. A suitable optical detection system could include, for example, a microscope (e.g., for brightfield, fluorescent, label-free multiphoton, or scanning electron microscopy). The detection system may be used to examine any characteristic of the cells housed within the assembly, such as cell shape, alignment, or protein expression (e.g., tight junction proteins).

Kits

The present invention provides kits for preparing an assembly. The kits comprise the membranes disclosed and further comprise one or more of the following: a luminal compartment, a subluminal compartment, a first cell, a second cell, an extracellular matrix hydrogel or an extracellular protein, media, a sealant, or any combination thereof.

The term "sealant" refers to any substance used to block the passage of fluids through the surface, joints, or openings in materials. As used herein, a "sealant" may also serve as an adhesive. For instance, in the Examples, the inventors used sterile PDMS to seal the components of the assembly together.

Cellular Assays

Additionally, the present invention provides methods for performing a cellular assay. The methods utilize a seeded elastic assembly comprising: a membrane comprising a plurality of pores therethrough, a luminal compartment housing a first cell, and a subluminal compartment housing a second cell as described herein. These components are assembled such that each of the luminal compartment, the subluminal compartment, and the membrane are mechanically coupled to each other and are capable of elastic deformation when a physiological stress is applied to a mechanically coupled anchoring member. In these methods, a seeded assembly or a system comprising a seeded assembling is assayed as to detect a characteristic of one or more cells that have been seeded into the assembly.

Suitable cellular assays include, without limitation, real-time assessment of cell shape and alignment, immunostaining and optical assessment of tight junction proteins, calcium transients measurement, electrical signal measurement, neurotransmitter signal measurement, trans-endothelial electrical resistance (TEER) measurement, and other permeability assessments. Advantageously, the assayed characteristics will be physiologically relevant in view of the modeled tissue. For instance, in the Examples, characteristics are used to assess the state of the model BBB before and after a TBI-associated disturbance. Cell shape and alignment are indicators of the cell population's status (i.e., healthy vs. diseased, quiescent vs. activated), while the TEER level, expression level of tight junction proteins, and the permeability value are all measures of the model's barrier function (i.e., its ability to regulate paracellular passage between adjacent cells).

These methods may further comprise applying a stimulus to the assembly. The stimulus may be a chemical stimulus (e.g., a drug, hormone, or toxin), an electrical stimulus, a mechanical stimulus, a paracrine stimulus from a nearby cell population, or any combination thereof. In some embodiments, the stimulus is a physiological stress, as described above. In these embodiments, membrane further comprises a mechanically coupled anchoring member, and the physiological stress is applied to the anchoring member, e.g., by an actuator.

In some embodiments, the first cell and/or the second cell is derived from a subject. In these embodiments, the detected characteristic may be indicative of the subject's response to the physiological stress or other stimulus. For instance, the assemblies may be seeded with cells derived from induced pluripotent stem cells (iPSC), allowing the devices to be used with patient-derived cells for personalized medicine applications. For example, human iPSC-derived microvascular endothelial cells, astrocytes, pericytes and neurons could be used to produce a personalized BBB-on-Chip, which would be a highly attractive model to test drug delivery across the BBB and to research treatments for secondary injuries of TBI, such as edema and inflammation.

Fabrication

Figure 6:
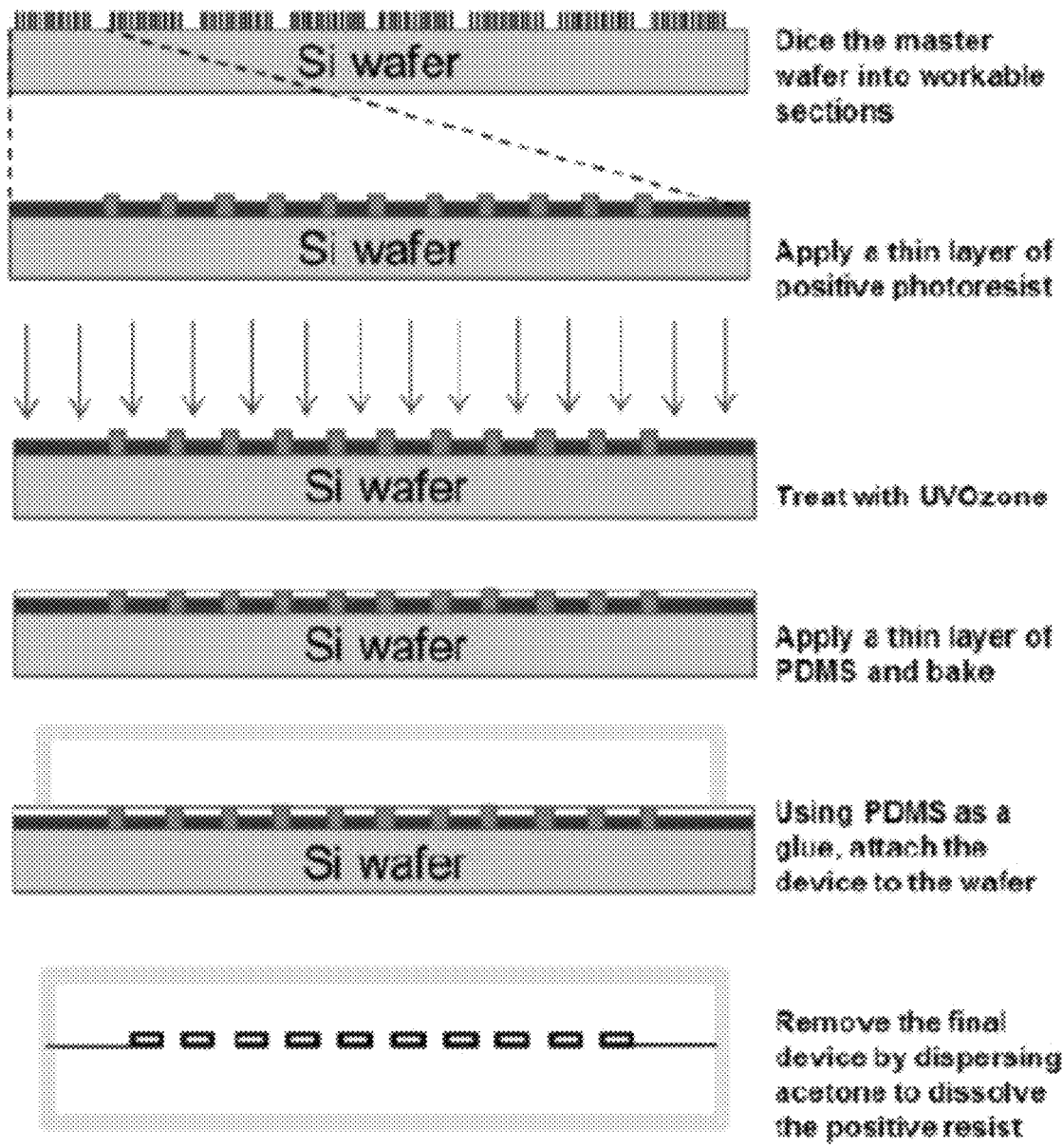
FIG. 6 shows a schematic for fabricating an elastic membrane

The present invention provides methods of making an elastic membrane. As illustrated in FIG. 6, the methods utilize a templating substrate comprising a plurality of pillars onto which a cured photoresist has been deposited such that the pillars extend through it. First, an elastomer is deposited on the cured photoresist such that the pillars extend through both the cured photoresist and the deposited elastomer. Then the elastomer is cured and coupled to an anchoring member. Finally, the cured photoresist is etched, thereby releasing a membrane comprising a plurality of pores therethrough mechanically coupled to an anchoring member.

Figure 7:
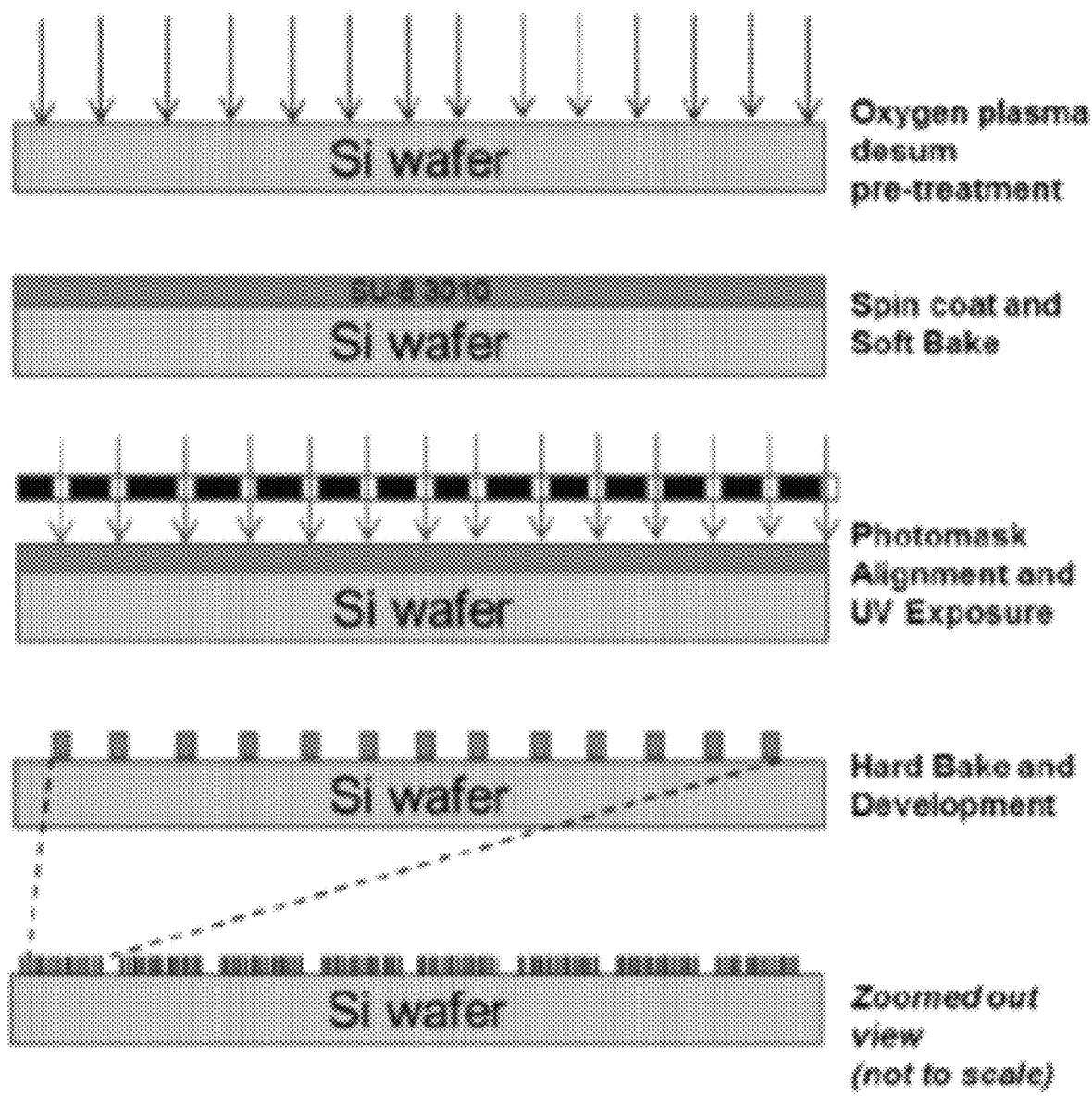
FIG. 7 shows a schematic for fabricating a templating substrate.
Figure 8:
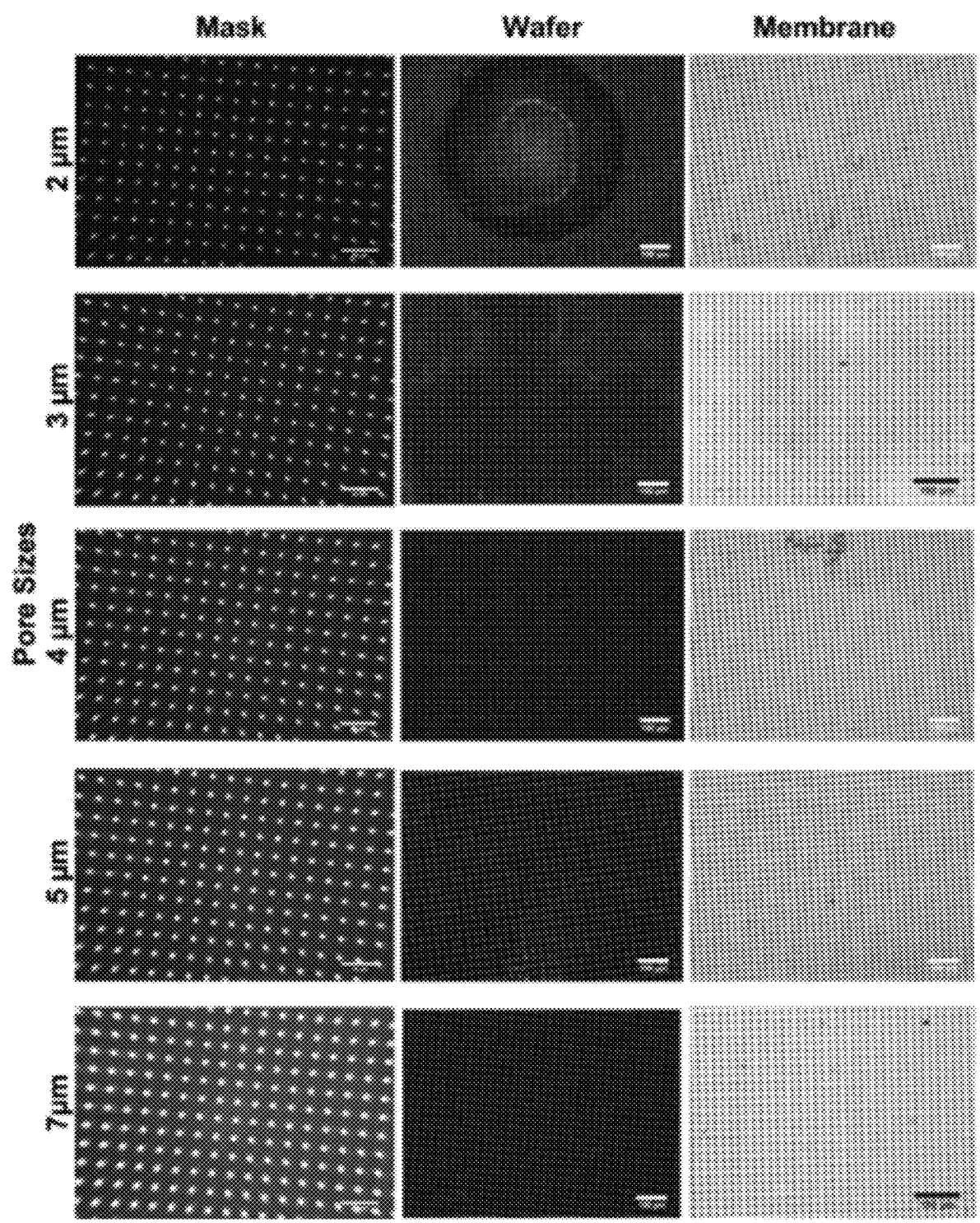
FIG. 8 shows stereoscope images of photomasks (mask), master wafers (wafer), and PDMS membranes (membrane) with post or pore sizes of 2-7 μm in diameter, spaced 25 μm center-to-center.

The term "templating substrate" refers to a surface that can be used as a mold for membrane fabrication. To create the membranes disclosed herein, the substrate must comprise pillars that are capable of forming appropriately sized pores. In the Examples, the templating substrate was fabricated from a silicon master wafer using photolithographic techniques (FIG. 7). In one embodiment, the wafer was designed to have 3 µm diameter pillars spaced 25 µm apart in a 5 mm×20 mm array of 12 µm tall cylindrical posts, as to cast membranes with 3 µm pores. However, it is not intended that the porous membrane of the invention be limited to a particular pore size or spacing. To adjust the pore size, one may simply print a mask with pillars that have a diameter of the desired pore size. For example, in other embodiments, the membranes have pore sizes ranging from 2 µm to 10 µm (FIG. 8).

As used herein, the term "photoresist" refers to a light-sensitive polymeric resin. Photoresists are formulated for use in photolithography, where they serve as masking materials for transferal of patterns to an underlying substrate via etching processes. In the present methods, the photoresist is used to form a sacrificial layer that can be etched away from beneath the cured elastomer, thus, freeing the newly formed membrane. As used herein, the term "etching" refers a process in which a layer (e.g., the photoresist) is chemically removed from a surface (e.g., the templating substrate). In the Examples, etching is accomplished using acetone. However, the etching step may be performed using any substance that can be used to wash away the chosen photoresist.

The membrane produced by these methods may be formed by the elastomer that is deposited on the cured photoresist. In the Examples, the elastomer is deposited by spin coating, such that it is applied in a uniform, thin coat. The elastomer may be any substance that will form membranes with the properties described herein. Importantly, the resulting membrane must be capable of elastic deformation when a physiological stress is applied to the anchoring member. In some embodiments, the elastomer is a polysiloxane, e.g., PDMS. The elastomer is cured by heating it to a sufficient temperature for a sufficient length of time. One of skill in the art will understand that the time and temperature required for curing will depend on the chosen elastomer. In the present methods, the removal of the membrane is aided by coupling the cured elastomer to an anchoring member, which forms a handle by which the membrane can be lifted from the templating substrate with a reduced likelihood of ripping. In the Examples, the inventors use a thin layer of PDMS as an adhesive that couples the cured elastomer to the anchoring member. However, coupling may be accomplished using any method by which the membrane and anchoring member can be firmly attached, and one of skill in the art will recognize that the ideal choice of coupling method will depend on the constitution of these components.

Traditionally, PDMS membranes have been fabricated by direct dry etching, direct UV-lithography [21], and standard soft-lithographic techniques [22, 23]. The first two methods require expensive equipment and in the third method, which requires a difficult membrane de-molding process, the membrane is frequently torn due poor mechanical properties of the thin membrane. Further, all three methods involve laborious process tweaking. To overcome these limitations, the inventors have developed methods described above for the fabrication of porous, thin (~10 µm), durable PDMS membranes with custom pore sizes as small as 2 µm. Importantly, these methods can be performed without manual handling of the membrane or the use of a carrier device (i.e., a device used to transport the membrane from the master wafer to the final device). Eliminating the need for careful manual removal of the membrane (e.g., with tweezers or via a carrier device) reduces the time and costs involved in the assembly of the chip. Thus, the provided making an elastic membrane represent a substantial improvement over the prior art.

The present invention also provides methods for preparing an elastic assembly for use in a cellular assay. The methods involve seeding a first compartment with a first cell, seeding a second compartment with a second cell, and coupling each of the compartments to an elastic membrane that comprises a plurality of pores and that is mechanically coupled to an anchoring member. Importantly, the components must be assembled such that each of the first compartment, the second compartment, and the membrane are capable of elastic deformation when the physiological stress is applied to the anchoring member. In these methods, the assembly may be prepared from a kit, such as those disclosed herein. The cells may be seeded in the compartments using any method known to those of skill in the art. In some embodiments, cells are seeded into the compartments before they are coupled to the membrane. In some embodiments, cells are seeded into the compartments before they are coupled to the membrane, e.g., by injection.

In some embodiments, the methods further comprise a step by which the assembly is integrated into a system. Specifically, the methods may further comprise (i) coupling an actuator to the anchoring member, (ii) fluidly coupling a pump with the first compartment, (iii) integrating a detection system with the assembly, (iv) or any combination thereof.

Examples

The following Example details the fabrication of a BBB-on-chip comprising a vascular compartment and a neural compartment. This chip provides a platform to study the blood-brain barrier following a non-penetrating traumatic brain injury (TBI). The present technology furthers TBI research by enabling the investigation of one or more of the following: the breakdown and dysfunction of the BBB following a mechanical insult, the repair of the BBB following a mechanical insult, the role fluid flow plays in facilitating or hindering BBB repair following a mechanical insult, the effect of multiple TBI's (i.e., with varied degree of the injury and the time between injuries) on the BBB integrity and function, the level of permeability that results a mechanical insult, the effect of circulating (e.g., blood-borne) molecules or toxins have on the BBB following a TBI, therapeutics that can mitigate TBI-induced BBB damage, the permeability of the BBB to therapeutics following a TBI, secondary effects of a TBI (e.g., cell swelling, calcium deregulation, inflammation, and cell death), permeabilization of the BBB via electroporation or the release of genetically modified brain capillary endothelial cells BBB-on-Chip Fabrication The devices disclosed herein offer cost and time advantages over previously used microfluidic systems built from silicon, as their fabrication is relatively easy, inexpensive, and highly reproducible. The bulk structures of the devices are fabricated by casting PDMS into reusable molds that can be manufactured using a 3D printer. These structures can be cleaned, sterilized and reused using methods such as sonication in 70% ethanol (v/v), perfusing the channel with 70% ethanol, autoclaving the chip for 10-15 minutes, and sterilizing with ultraviolet (UV) light. Additionally, the master wafers used in the fabrication of the porous membrane can be reused up to 5 times, saving time and money.

Compartments

Figure 9B:
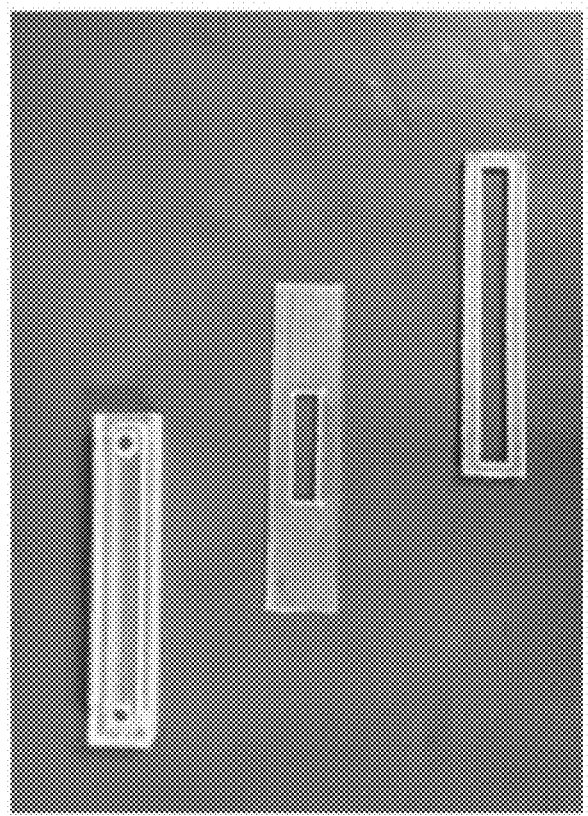
FIG. 9A-9B shows photographs of the reusable, 3D-printed molds (FIG. 9A) and BBB-on-Chip parts produced from the molds (FIG. 9B). To produce BBB-on-Chip parts, PDMS was cast into the molds and allowed to cure before removal.
Figure 9A:
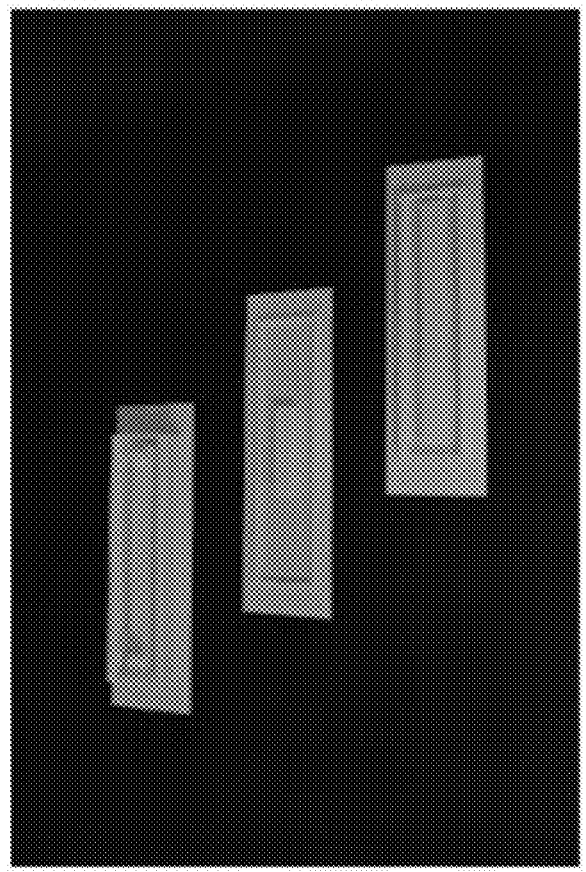

The vascular and neural compartments (FIG. 9B) of the chip were created by casting 10:1 polydimethylsiloxane (PDMS) into reusable templates (FIG. 9A) that were printed out of acrylonitrile butadiene styrene (ABS) on a 3D printer. PDMS was also used as an adhesive to attach the luminal compartment, elastic membrane, anchoring member, and subluminal compartment.

Master Wafer

Silicon wafers (76.2 mm in diameter, 380 μm thick, <100> oriented, single side polished) are sterilized in the LFE APE-110 Asher. SU-8 (MicroChem) is then deposited on the wafer and spun to create a 12 μm thick layer according to the spincoating recipe in Table 1. The wafer is then baked on a hotplate set at 95° C. for 8 minutes. After allowing time for the wafer (coated in photoresist) to cool, the wafer and mask are mounted onto a MJB3 contact aligner. The photoresist is then exposed to 187.5 mJ/cm$^2$ of UV light. In one trial, the mask was designed to create 3 μm diameter posts spaced 25 μm in a 5 mm×20 mm array. In other trials, membranes with pore sizes ranging from 2 μm to 10 μm were created by printing a mask in which the transparent circles had a diameter of the desired pore size. A post-exposure bake is done for 1 min at 65° C. and 3 minutes at 95° C. After the post-exposure bake, the wafer is developed using SU-8 developer (MicroChem) and rinsed with isopropyl alcohol (IPA). To maintain the stability of the pillars, the master wafer is hard baked for 15 minutes at a temperature between 150-200° C. Lastly, the wafer is cut using a K&S 982-10S Dicing Saw to separate each array, into a working section.

TABLE 1

Spin coating recipe for a 12 μm thick SU-8 3010 layer.

| Step | Ramp | RPM | Dwell |
| --- | --- | --- | --- |
| 1 | 1.0 | 500 | 10 |
| 2 | 1.0 | 2000 | 30 |

Membrane Layers

The workable sections of the master wafer are coated with a thin layer (<1 μm) of positive photoresist according to the spin coating recipe of Table 2. Once the positive resist is completely cured, a thin layer of PDMS is deposited on top of the positive resist according to the spin coating recipe of Table 3. The positive photoresist acts as a sacrificial layer, for the easy removal of the porous membrane from the working section.

TABLE 2

Spin coating recipe for the coating of positive photoresist onto the working section of the master wafer.

| Step | Ramp | RPM | Dwell |
| --- | --- | --- | --- |
| 1 | 1.0 | 500 | 15 |
| 2 | 1.0 | 6000 | 30 |

TABLE 3

Spin coating recipe the coating of PDMS onto the working section of the master wafer.

| Step | Ramp | RPM | Dwell |
| --- | --- | --- | --- |
| 1 | 5.0 | 500 | 5 |
| 2 | 5.0 | 1000 | 5 |
| 3 | 10.0 | 3000 | 10 |
| 4 | 10.0 | 6000 | 60 |
| 5 | 10.0 | 2000 | 15 |
| 6 | 10.0 | 1000 | 10 |
| 7 | 5.0 | 500 | 5 |

This configuration requires that the combined height of the positive resist and the PDMS must be shorter than the height of the cylindrical pillars. The thickness of the membrane can be varied, if it is confirmed that the pores penetrate completely through the membrane. Once the PDMS is cured, a thin layer of PDMS is used to fuse the elastic membrane of the chip to the cured PDMS layer. Acetone is used to wash away the positive photoresist allowing for easy lift-off of the PDMS membrane from the wafer using the attached middle layer as a handle.

The middle layer and attached membrane are then adhered to an anchoring member composed of silicone sheeting, followed by the cellular compartments, all via PDMS bonding. Notably, in embodiments in which a closed-base compartment is utilized (e.g., for TEER measurements), the compartment is only attached after the cells have been seeded.

Cell Seeding and Assembly

Rat brain microvascular endothelial cells (RBMEC, ScienCell Research Laboratories) were cultured in Endothelial Cell Medium-rat (ECM-r, ScienCell Catalog #1021) supplemented with 5% calf serum (ScienCell, Catalog #0025-cs)

and 1% Endothelial Cell Growth Supplement-rat (ECGS-r, ScienCell Catalog #1062). Cells were incubated at 37° C., 95% humidity and 5% $CO_2$ until confluent. Primary rat astrocytes were isolated from the cortex of neonatal day–1 rat pups using modified published methods [24].

Astrocytes were seeded in Matrigel® Matrix (Corning, Corning, NY), which provided both cell types with neurovascular basement membrane proteins needed for attachment, growth, and viability. The thickness of elastic membrane results in a divot beneath the porous membrane. A thin layer (10 μL) of Corning Matrigel Matrix, Phenol Red Free was spread within the divot and set in the incubator to polymerize. The neural compartment was then attached using sterile PDMS as the adhesive, and the chip was set back in the incubator for 1 hour to cure the PDMS. ECM-r or astrocyte conditioned media is then injected into the neural compartment to rehydrate the Matrigel. RBMECs were then tryspinized from their culture flask and 50,000 cells were seeded directly onto the porous membrane.

In some trials, astrocytes were included in the neural compartment as a suspension in the hydrogel. Here, primary rat astrocytes were trypsinized from their culture flask and 50,000 astrocytes were resuspended in 50 μL of Matrigel. This suspension was spread within the divot and set in the incubator to polymerize. The neural compartment was then attached to the elastic membrane. To keep the astrocytes hydrated, a small amount of media was used to cover the Matrigel during the PDMS curing time. Astrocyte culture media was then injected into the neural compartment. Finally, RBMECs are tryspinized from their culture flask and 50,000 cells are seeded directly onto the porous membrane. If initial RBMEC attachment is poor (i.e., the cells do not form a confluent monolayer within 5 days), another round of cells is seeded 5-8 days after the initial seeding.

Once cell seeding is complete, tubing is added at the media inlet and outlet ports to form a mechanotransductive BBB-on-Chip).

Fluid Flow

The BBB-on-Chip was designed to allow medium to flow through the vascular compartment, imposing a fluid shear stress across the microvascular endothelial cells (MVECs) that mimics the steady, laminar fluid shear stress imposed by blood circulation through the BBB. Capillary shear stress is approximately 6.2 dynes/$cm^2$ [25].

To calculate the required inlet flow rate to achieve this desired shear stress in the BBB-on-Chip the following equation was used: $Q=\tau a2b/6\mu$, where Q is the volumetric flow rate in mL/min, t is the fluid shear stress in dynes/$cm^2$, a is the height of the channel in cm, b is the width of the channel in cm, and μ is the dynamic viscosity of the fluid (DMEM) in dynes/$cm^2$. Once the MVECs in the chip reach confluency across the porous membrane, the fluid shear stress within the chip was built up until it reached a capillary-like level (i.e., 2.5 dynes/$cm^2$, followed by 4 dynes/$cm^2$, and then 6.2 dynes/$cm^2$ for 24 hours each). A peristaltic pump and dampener are used to keep the flow continuous and create a smooth flow profile (See FIG. 4 for a schematic of the flow system).

Traumatic Brain Injury Simulation

Since the fabricated chip is entirely elastic, it can be subjected to a uniaxial, biaxial, or a multiaxial strain using tension devices, pressure pulses, or a vacuum. An in-house cell-stretching device, referred to as high-speed cell stretcher, was utilized to stretch the BBB-on-Chip. The chip is subjected to stretching by bracing the anchoring member within metal clamps, mounting the chip onto the high-speed cell stretcher, and programming the stretcher to uniaxially displace the chip to the desired percent stretch at a desired stretch rate.

An Electrode System to Measure TEER

To measure the electrical resistance across the MVEC monolayer, electrodes were incorporated within the chip to make trans-endothelial electrical resistance (TEER) measurements (FIG. 5). The electrodes were embedded in the chip above and below the porous membrane and connected to an electrode adaptor for the Epithelial Volt/Ohm (TEER) Meter EVOM2 (World Precision Instruments). With this setup, 0.008" diameter Ag/AgCl electrodes (A-M Systems) deliver current through the cell monolayer or co-culture and 0.1 mm diameter Ag wires (Sigma Aldrich) measure the voltage across the monolayer or co-culture. The EVOM2 converts the voltage reading to resistance values. To measure the TEER, the baseline TEER (TEER of a chip with no cells) is subtracted from the measured TEER value to give a normalized TEER value.

BBB Model Validation

Figure 10B:
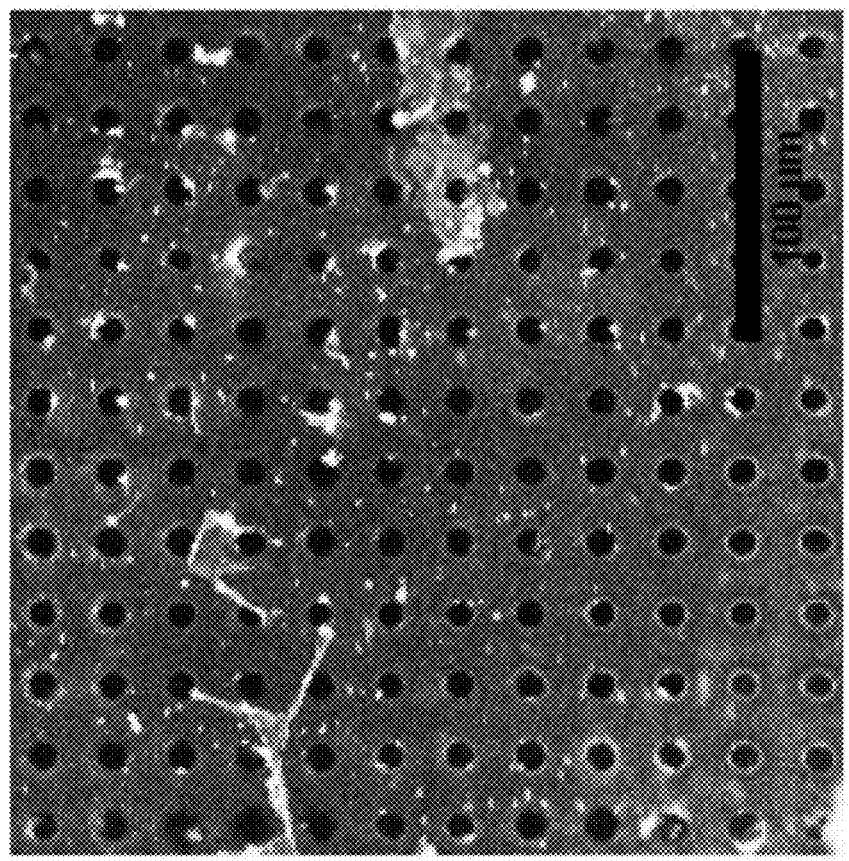
FIG. 10A-10B show images of a porous membrane with 3 μm diameter pores spaced 25 μm apart center-to-center.
Figure 10A:
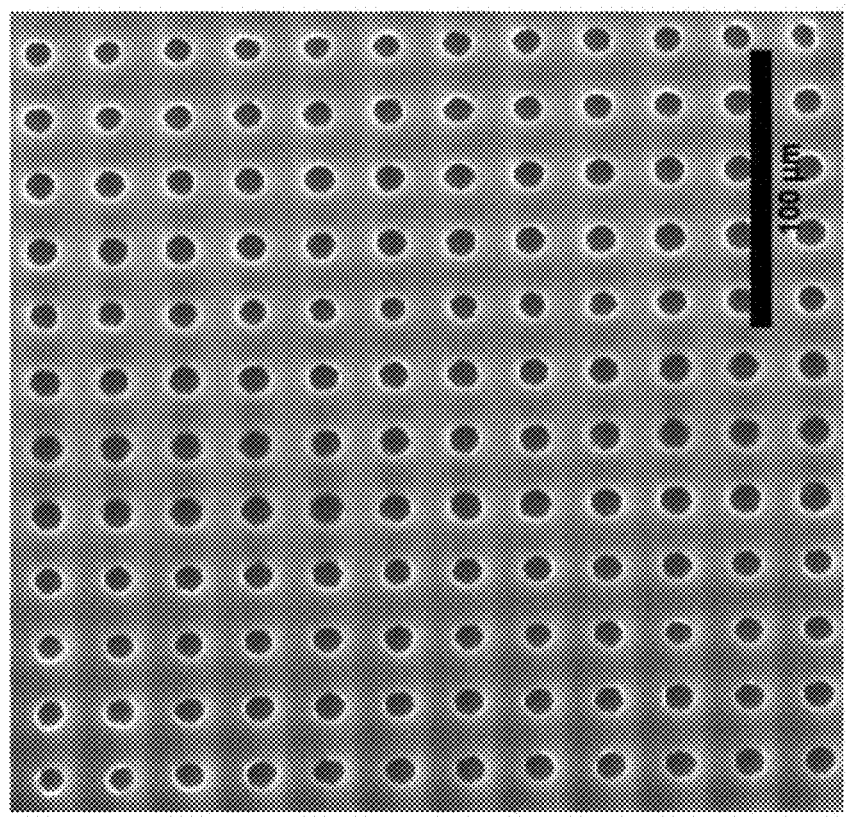

Several assessments were performed to validate the BBB-on-Chip as a platform that models the blood brain barrier (BBB). First, to allow for crosstalk between cells in the upper and lower compartments of the chip, we assessed the size and completeness of the pores in the porous membrane. The PDMS membrane was imaged using an Environmental Scanning Electron Microscope (ESEM) and Multiphoton Microscope. Images taken from a membrane with 3 μm diameter pores spaced 25 μm apart center-to-center are provided in FIG. 10A-10B. These images demonstrate that the fabrication method resulted in complete pores throughput the membrane.

Figure 11A:
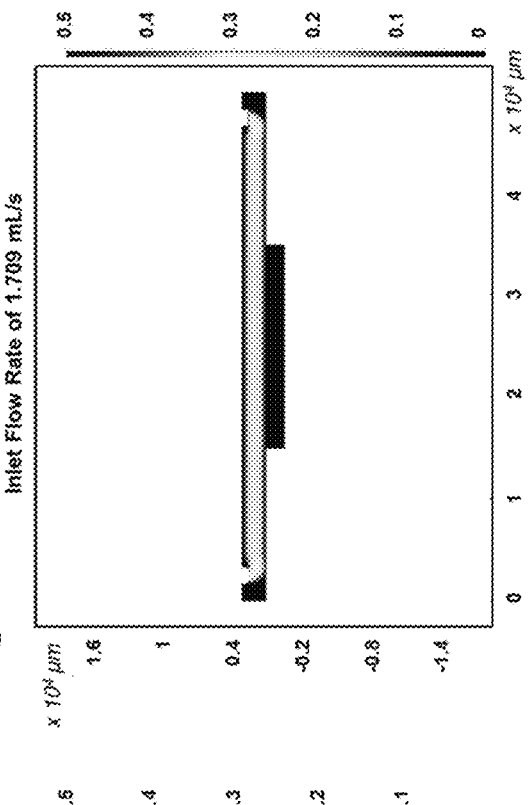
FIG. 11A-11C show plots of the fluid flow through the BBB-on-Chip with inlet flow rates of 1.068 mL/s (FIG. 11A), 1.709 mL/s (FIG. 11B), and 2.650 mL/s (FIG. 11C). The color scale is in units of m/s.
Figure 11B:
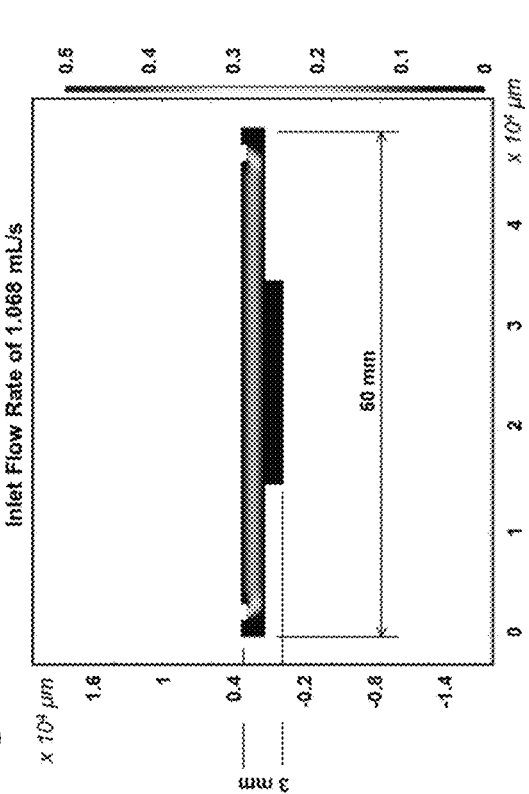
Figure 11C:
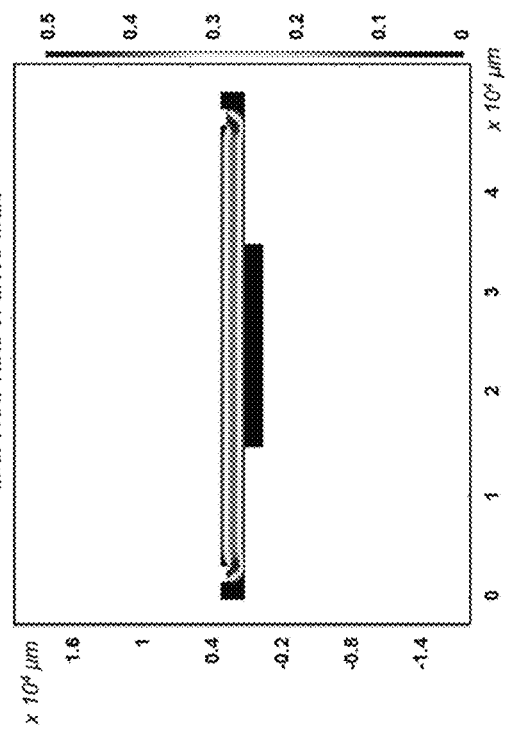
Figure 12:
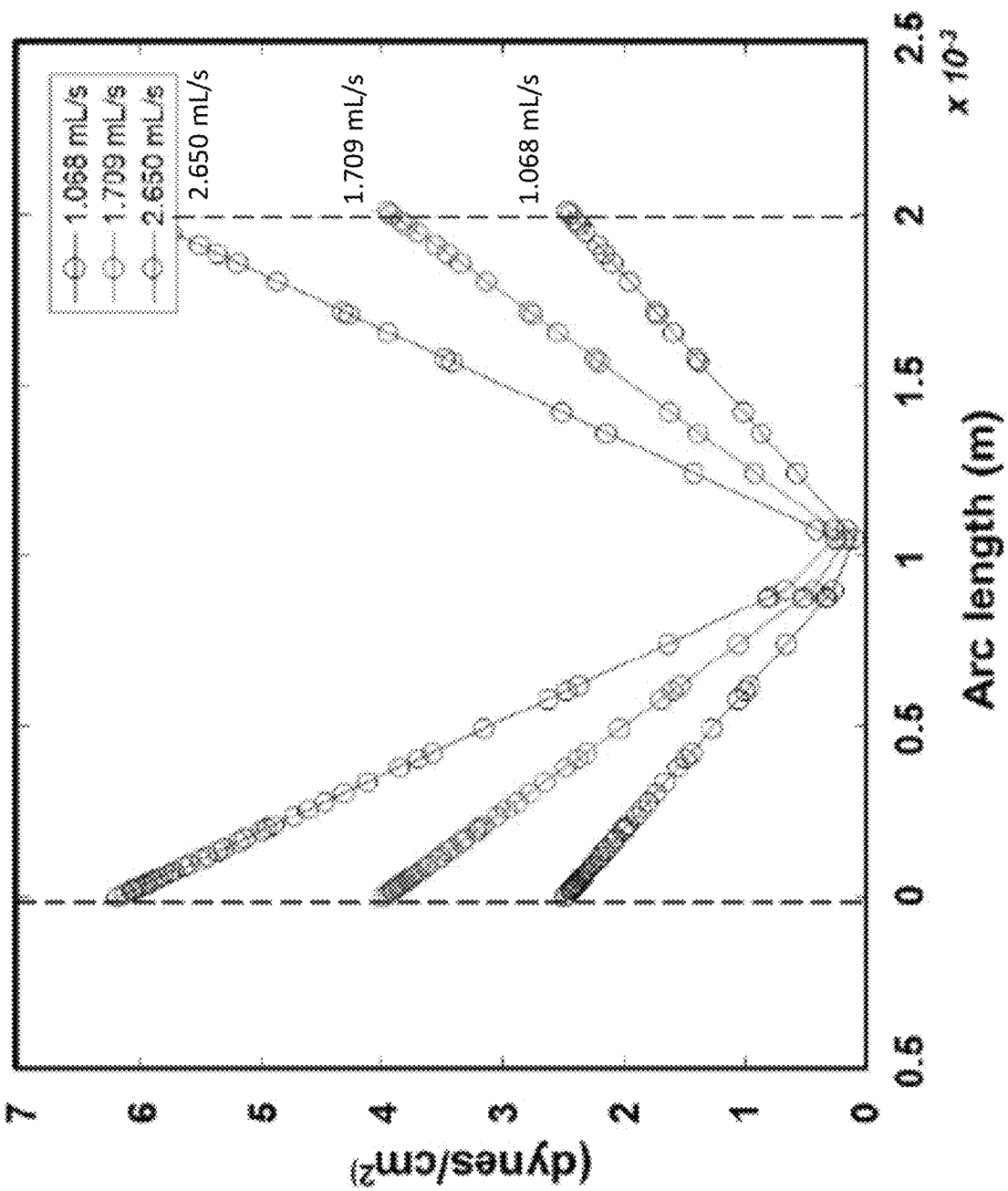
FIG. 12 shows a graph depicting the shear stress profile for the capillary flow through the BBB-on-Chip at three flow rates.
Figure 13B:
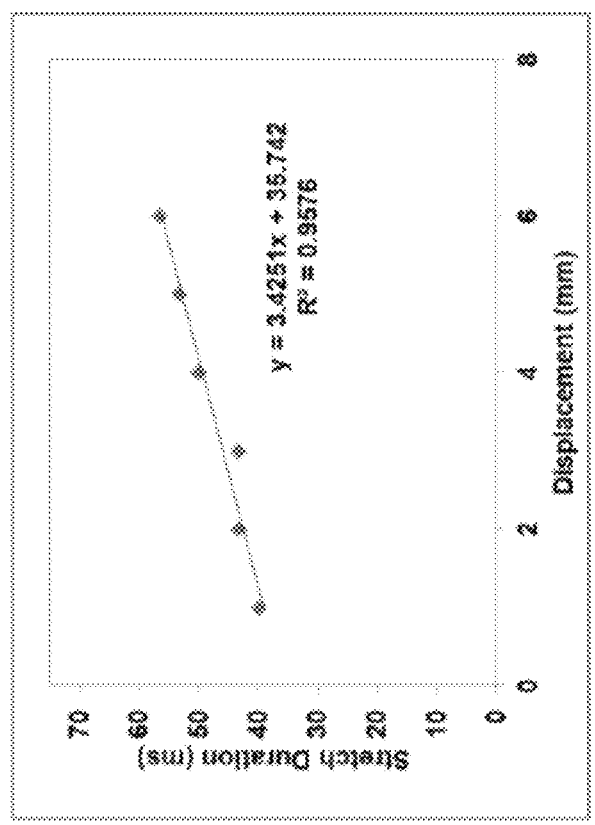
FIG. 13A-13B show graphs characterizing the high-speed stretch device for use with the BBB-on-Chip.
Figure 13A:
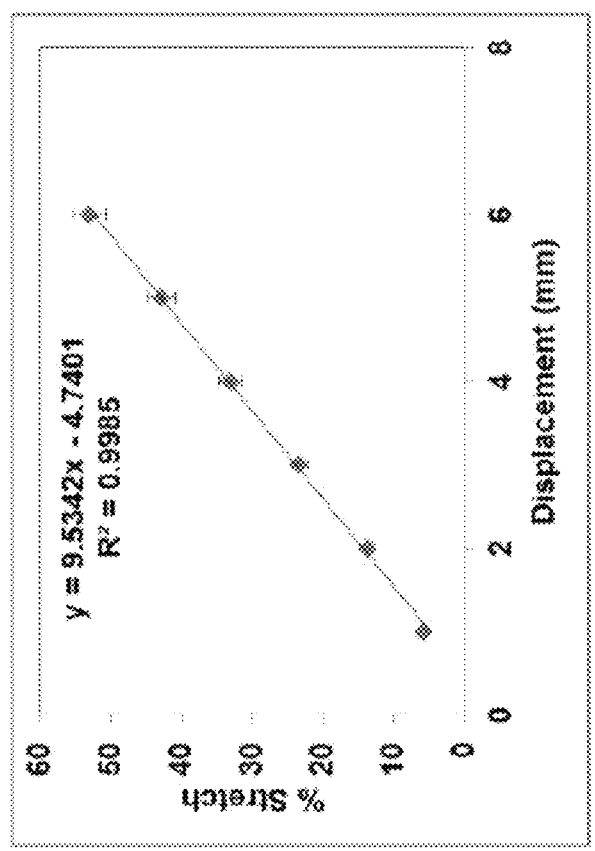

Next, we verified that the calculated volumetric fluid flow rates would achieve the desired fluid shear stress at the wall of the chip (i.e., where the MVECs are positioned). Volumetric flow rates were calculated to achieve fluid shear stress values of 2.5 dynes/$cm^2$, 4 dynes/$cm^2$, and 6.2 dynes/$cm^2$, as described above in the section titled "Fluid Flow". The chip was drawn to scale in the computer-aided design software AutoCAD® and uploaded to Comsol Multiphysics® 5.3 modeling software. A two-dimensional simulation was run to produce the fluid velocity profile and corresponding velocity colormaps. Using a custom MATLAB script, the velocity profile was plotted (FIG. 11A-11C) and the equation $\tau=(du/dx)\mu$ was used to plot the shear rate and shear stress profiles. In the equation above, t is the fluid shear stress, du/dx is the shear rate, and u is the dynamic viscosity. FIG. 12 shows that the shear stress values of 2.5 dynes/$cm^2$, 4 dynes/$cm^2$, and 6.2 dynes/$cm^2$ were achieved for a volumetric flow rate of 1.068 mL/s, 1.709 mL/s, and 2.650 mL/s, respectively.

For these experiments, substrates were created by spin coating 25 mm no. 1 coverslips with polydimethylsiloxane (PDMS) Sylgard® 184 (Dow Corning, Midland, MI) and Sylgard® 527 (Dow Corning) in varying ratios (Table 4) to obtain compliant or stiff substrates. The tangent modulus of compliant and stiff substrates was measured using standard uniaxial mechanical testing protocols from 5 different samples prepared on two different days. Briefly, 2 mm thick tensile strips were cut and uniaxially stretched at 2 mm/min, until failure using Instron 5900 Series (Canton, MA). Sample tangent moduli of these samples were quantified from the linear region of the stress strain curves. The compliant matrices had a modulus of 4.98+0.51 kPa and the stiffer matrices had a modulus of 88.32+10.06 kPa.

TABLE 4

Spin coating recipe the coating of PDMS onto the working section of the master wafer.

|  | Sylgard 527 A:B in 1:1 ratio | | Sylgard 184 Base:Curing in 10:1 ratio | | |
| --- | --- | --- | --- | --- | --- |
|  | A | B | Base | Curing Agent | Total |
|  | | | Amount (%) | | |
| Compliant substrate | 49.4 | 49.4 | 1.1 | 0.1 | 100 |
| Stiff substrate | 41.8 | 41.8 | 14.9 | 1.5 | 100 |

Figure 14:
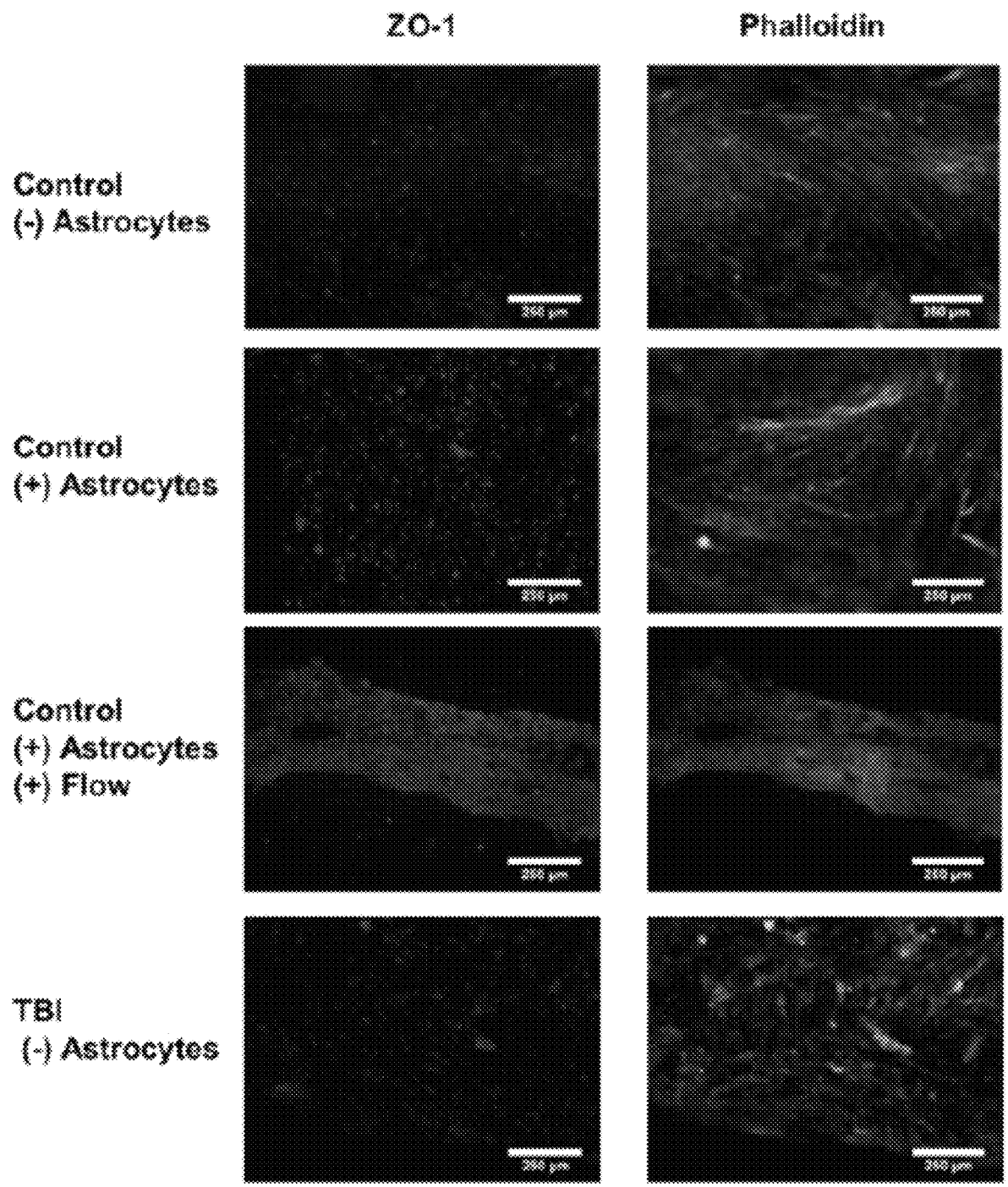
FIG. 14 shows fluorescent images of ZO-1 expression and the actin cytoskeleton stained by phalloidin in the BBB-on-Chip. Nuclei are stained with DAPI.
Figure 15:
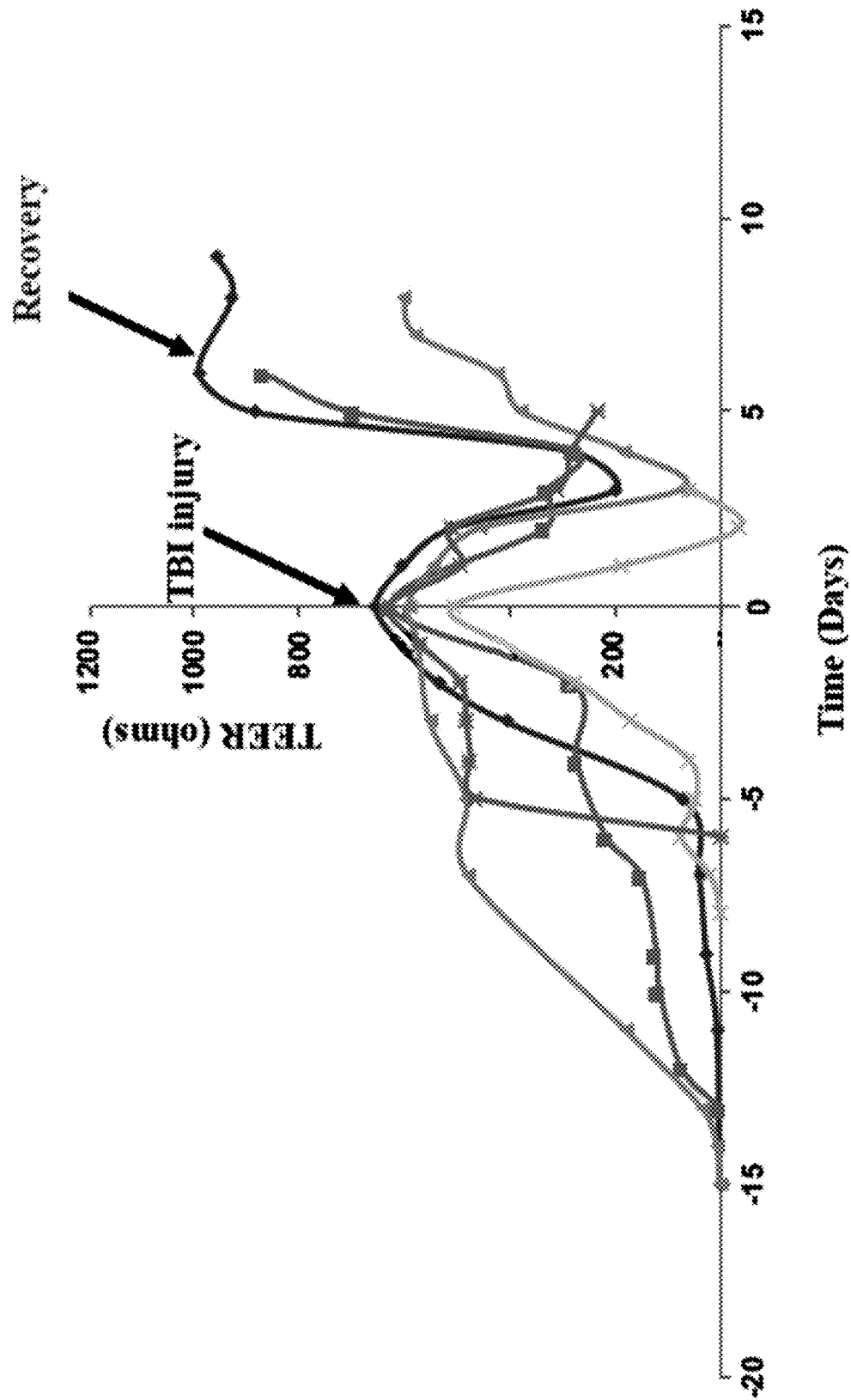
FIG. 15 shows a graph of TEER measurements taken on five separate BBB-on-Chips before and after TBI simulation. Cells were seeded on the chips 5-15 days before TBI simulation.

Additionally, we confirmed that the chip could be subjected to a stretch with a TBI-like magnitude and rate. To this end, 50 µL of Matrigel® Basement Membrane Matrix (Corning, Corning, NY) was spread evenly along the porous membrane. The Matrigel® was polymerized for 20 minutes at 37° C., and the top of the gel was marked with a 3×10 point grid. The chip was then mounted on the stretching device and we recorded the displacement of the marker grid during 1, 2, 3, 4, 5, and 6 mm programmed stretch using a Basler a640 area-scan camera at 300 frames per second. Using a custom MATLAB script, we tracked the motion of the marker grid and calculated the mean percent stretch within each element of the grid for each displacement. We plotted the percent stretch versus motor displacement (FIG. 14A) and recorded the duration for each of the 6 displacements (FIG. 14B). Our previous studies suggest that a non-penetrating injury occurs within 50 milliseconds, and that a mild TBI stretch has a magnitude of 10-25%, a while a moderate stretch has a magnitude of 25-50%, and a severe stretch has a magnitude of greater than 50%. The results of this analysis demonstrate that our mechanotransductive BBB-on-chip can be subjected to a mild and moderate TBI. However, by optimizing our stretch bioreactor or reducing the size of the chip, the chip could be subjected to a stretch of greater magnitude.

We demonstrated that our chip shares important characteristics with the BBB. Specifically, we showed that the MVECs had a high expression of tight junction proteins (FIG. 14), that the TEER level rose with cell confluency and culture time, and that damage to the model BBB (induced via stretching) reduced the measured TEER level (FIG. 16). Together, these observations demonstrate that the chips provided herein are representative models of the BBB.

Oscillatory Flow

Figure 16D:
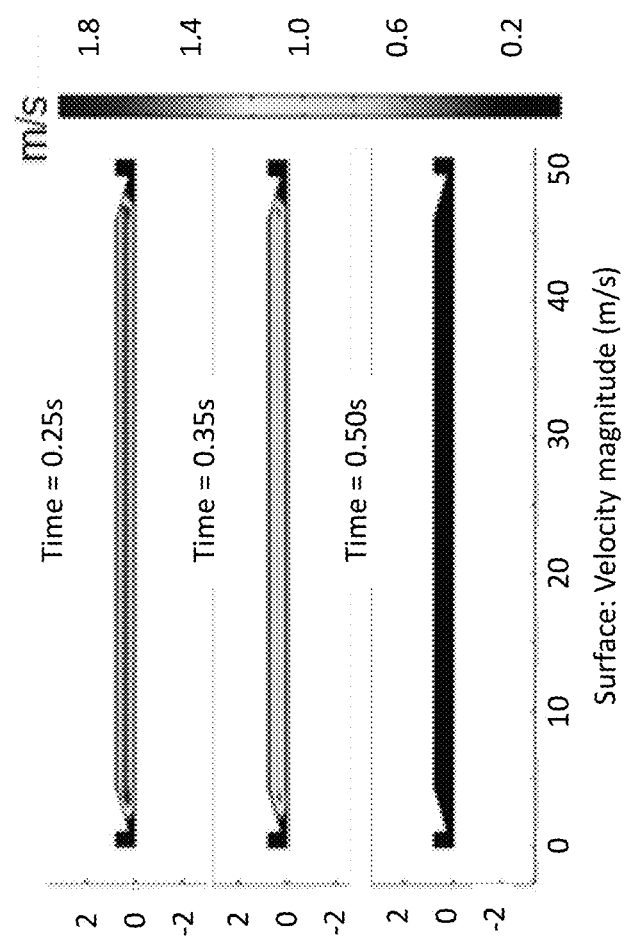
Figure 16C:
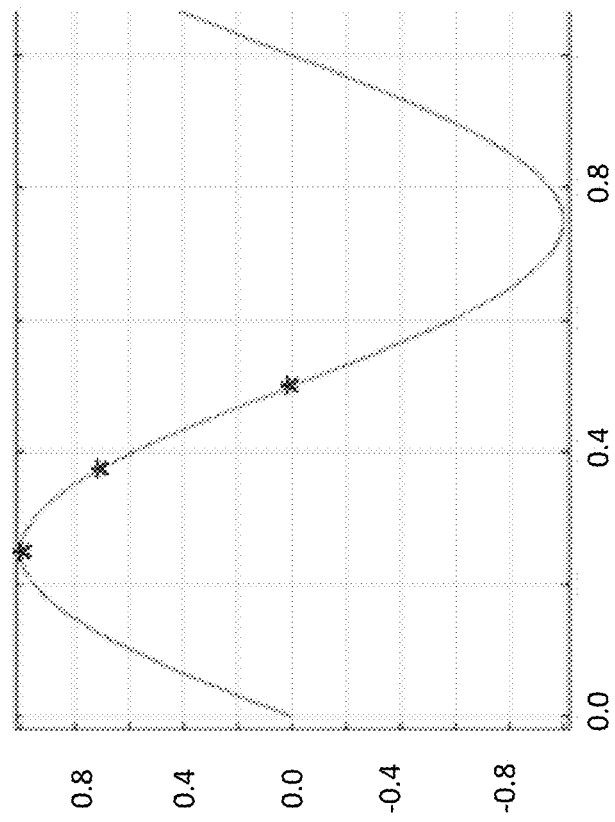
Figure 16E:
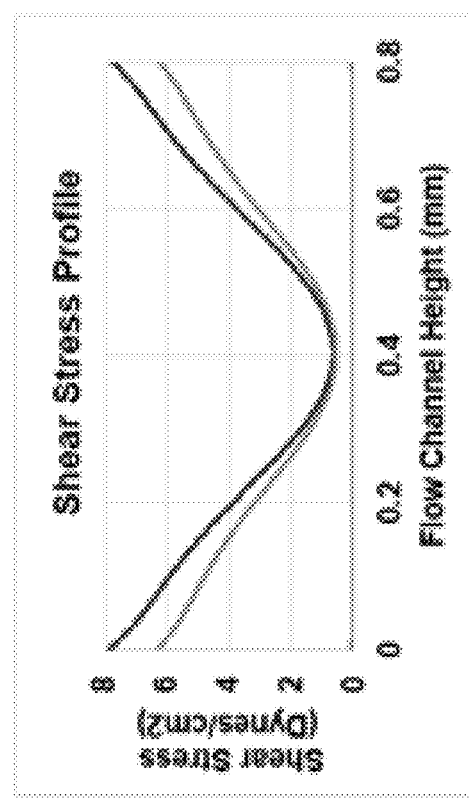
Figure 16F:
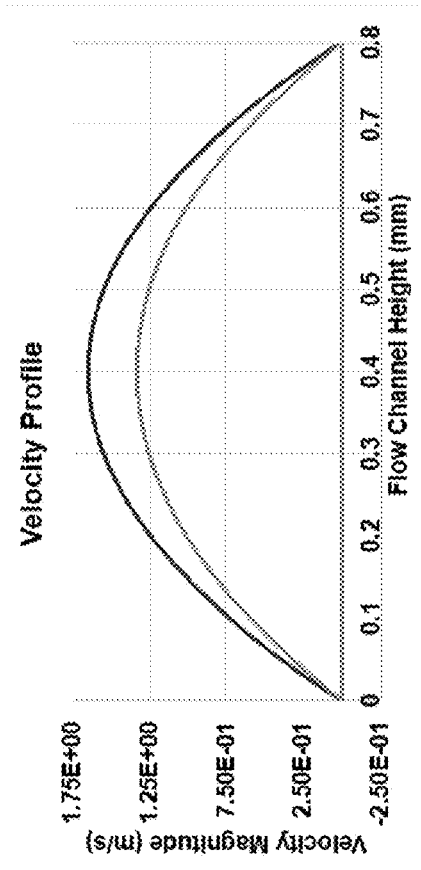

We present here data demonstrating the use of our platform to stimulate cells with oscillatory flow patterns. BBB chips were constructed as outlined above. The elastic membrane was marked with a fiducial array of dots and subject to high-speed imaging to capture the deformation of the dot array in our stretching platform (FIG. 16A-16B). We also simulated oscillatory flow in our chip (FIG. 16C-16F) using COMSOL to determine if we were able to obtain a time-varying laminar, parabolic flow profile within the chip for the entire duration of the oscillatory flow cycle. Note the altered angular geometry of the inlet into the chip (FIG. 1d) compared to the initial provisional filing. We determined that the angular inlet ensured more uniform flow and less stagnation at the inlets and outlets.

Differentiated Human Induced Pluripotent Cells (hiPSC)

Figure 17A:
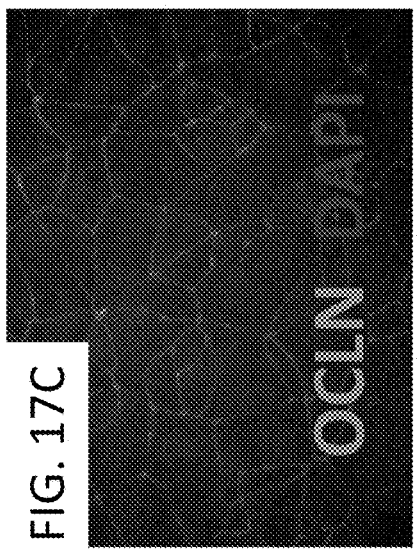
FIG. 17A-17C shows differentiation of hiPSCs into brain microvascular endothelial cells. Immunostaining shows (FIG. 17A) claudin 5.
Figure 17B:
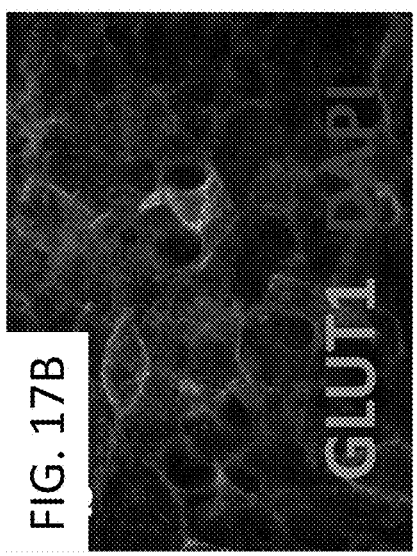
Figure 17C:
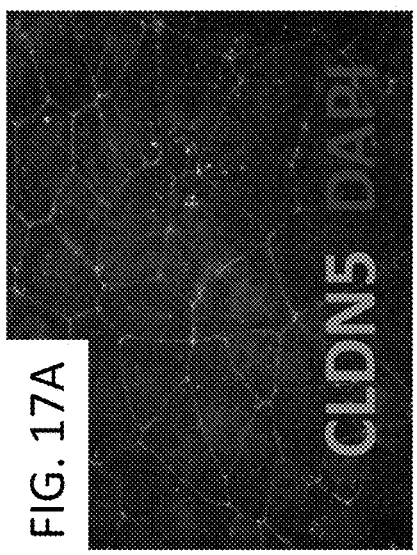

We have differentiated human induced pluripotent cells (hiPSC) into brain microvascular endothelial cells (BMECs) and have cultured them in our BBB-chip platform (FIG. 17). These cells were then subject to traumatic brain injury and trans-endothelial electrical resistance (TEER) was monitored for 7 days post-TBI.

BMEC differentiation protocols were primarily taken from a recently published paper that provides reproducible, efficient differentiation of iPSCs to BMECs (Neal E H et al. A Simplified, Fully Defined Differentiation Scheme for Producing Blood-Brain Barrier Endothelial Cells from Human iPSCs. Stem cell reports. 2019; 12 (6): 1380-8.). iPSCs were maintained in E8 medium (ThermoFisher) on Matrigel (Corning) coated plates. For differentiation, single cell suspensions were seeded in E8 medium with the addition of Y-27632 (Torcis) on Matrigel coated plates for 24 hours at a density of 16,000 cells/cm$^2$. Following 24 hours, E8 medium was removed and E6 media (ThermoFisher) was used for 4 days, with medium changes every 24 hours. Following the 4th day of E6 medium, E6 was aspirated and replaced with human endothelial serum free medium (ThermoFisher) with bFGF (PeproTech), retinoic acid (RA) (Sigma) and B27 supplement (ThermoFisher). Medium was not changed for 48 hours. After 48 hours, cells were lifted with accutase and seeded onto the chip platform that was plasma activated and pre-coated with collagen IV (Sigma) and fibronectin (Sigma) overnight. Following 24 hours, bFGF and RA were removed from the media and trans-endothelial electrical resistance (TEER) was measured using our custom electrode setup, to check endothelial cell barrier resistance. 24-48 hours following differentiation, TEER readings should be between 1500-2000 $\Omega \cdot cm^2$. Samples were immunostained against claudin-5 (CLDN5), glut-1 and occludin (OCLN), counterstained with DAPI and imaged using an epifluorescence microscope.

Figure 18:
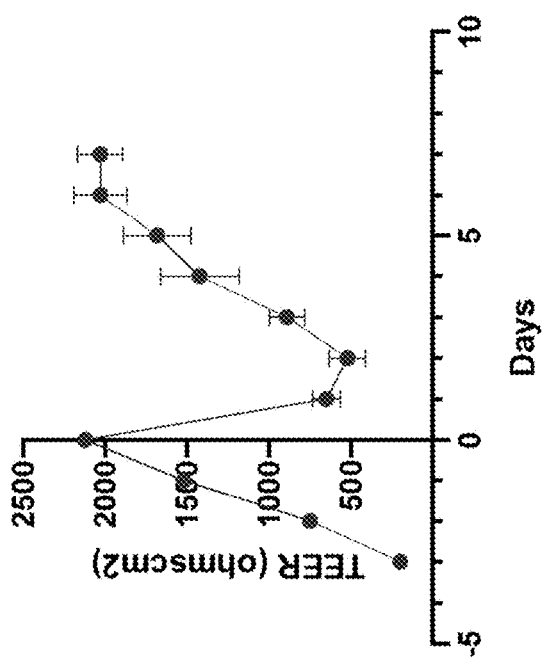
FIG. 18 shows longitudinal TEER measurements of hiPSC-derived BMECs in our organ-chip system (n=4).

Once 1500-2000 $\Omega \cdot cm^2$ was achieved, samples were then subject to TBI in our high-speed stretching platform. TEER was read every 24 hours for 7 days post-TBI and reported. Our results (FIG. 18) showed an acute decrease in TEER immediately following TBI (t=0 days) over 48 hours, followed by an increase (i.e., recovery) in TEER thereafter. Our results demonstrate our ability to develop a stable human BMEC barrier that we can reliably subject to TBI. This data shows that our platform can be used to study BBB integrity following injury and also for the development of a potential therapeutic window for treatment of edema post-TBI.

REFERENCES

[1] D. R. Namjoshi, C. Good, W. H. Cheng, W. Panenka, C. P. A. D. Richards and C. Wllington, "Towards clinical management of traumatic brain injury: a review of models and mechanisms from a biomechanical perspective," Disease Models & Mechanisms, pp. 1325-2338, 2013.

[2] Center for Disease Control and Prevention, "Traumatic Brain Injury and Concussion," [Online]. Available: https://www.cdc.gov/traumaticbraininjury/get_the_facts.html. [Accessed 27 Apr. 2017].

[3] I. Humphreys, R. L. Wood, C. J. Phillips and S. Macey, "The costs of traumatic brain injury: a literature review," Clinicoeconomics and Outcomes Research, vol. 5, pp. 281-287, 2013.

[4] B. V. Zlokovic, "The Blood-Brain Barrier in Health and Chronic Neurodegenerative Disorders," Neuron, vol. 57, pp. 178-201, 2008.

[5] A. D. Wong, M. Ye, A. F. Levy, J. D. Rothstein, D. E. Bergles and P. C. Searson, "The blood-brain barrier: an engineering perspective," Frontiers in Neuroengineering, vol. 6, no. 7, pp. 1-22, 2013.

[6] B. Obermeier, R. Daneman and R. M. Ransohoff, "Development, maintenance, and disruption of the blood-brain barrier," Nature Medicine, vol. 19, no. 12, pp. 1584-1596, 2013.

[7] M. van der Helm, A. van der Meer, J. Eijkel, A. van der Berg and L. Segerink, "Microfluidic organ-on-chip technology for blood-brain barrier research," Tissue Barriers, vol. 4, no. 1, 2016.

[8] E. Vandenhaute, A. Drolez, E. Sevin, F. Gosselet, C. Mysiorek and M. Dehouck, "Adapting coculture in vitro models of the blood-brain barrier for use in cancer research: maintaining an appropriate endothelial monolayer for the assessment of transendothelial migration," Laboratory Investigation, vol. 96, pp. 588-598, 2016.

[9] L. Yang, K. Shah and Abbruscato, "An In Vitro Model of Ischemic Stroke," Astrocytes, vol. 214, pp. 451-466, 2011.

[10] L. Cucullo, N. Marchi, M. Hossain and J. D., "A Dynamic in vitro BBB Model for the Study of Immune Cell Trafficking into the Central Nervous System," Journal of Cerebral Blood Flow & Metabolism, vol. 31, no. 2, 2010.

[11] L. Xiao-Dong, Y. Zhi-Hong and Y. Hiu-Wen, "Repetitive/temporal hypoxia increased P-glycoprotein expression in cultured rat brain microvascular endothelial cells in vitro," Neuroscience Letters, vol. 432, no. 3, pp. 184-187, 2008.

[12] N. J. Abbott, L. Ronnback and E. Hansson, "Astrocyte-endothelial interactions at the blood-brain barrier," Nature Reviews Neuroscience, vol. 7, pp. 41-53, 2006.

[13] M. Blanchette and R. Daneman, "Formation and maintenance of the BBB," Mechanisms of Development, vol. 138, pp. 8-16, 2015.

[14] B. R. Flachsbart, K. Wong, J. M. Iannacone, E. N. Abante, R. L. Vlach, P. A. Rauchfuss, P. W. Bohn, S. J. V. and M. Shannon, "Design and fabrication of a multilayered polymer microfluidic chip with nanofluidic interconnects via adhesive contact printing," Lab on a Chip, vol. 6, no. 5, pp. 667-674, 2006.

[15] A. Epshteyn, S. Maher, A. Taylor, A. Holton, B. J. T. and J. Cuiffi, "Membrane-integrated microfluidic device for high-resolution live cell imaging," Biomicrofluidics, vol. 5, no. 4, 2011.

[16] J. Kawada, H. Kimura, H. Akutsu, Y. Sakai and T. Fujii, "Spatiotemporally controlled delivery of soluble factors for stem cell differentiation," Lab on a Chip, vol. 12, no. 21, pp. 4508-15, 2012.

[17] C. Sip and A. Folch, "Stable chemical bonding of porous membranes and poly(dimethylsiloxane) devices for long-term cell culture," Biomicrofluidics, vol. 8, no. 3, 2014.

[18] K. Aran, L. Sasso, N. Kamdar and J. Zahn, "Irreversible, direct bonding of nanoporous polymer membranes to PDMS or glass microdevices," Lab on a Chip, vol. 10, no. 5, pp. 548-555, 2010.

[19] B. Chueh, D. Huh, C. Kyrtsos, T. Houssin, F. N. and S. Takayama, "Leakage-Free Bonding of Porous Membranes into Layered Microfluidic Array Systems," Analytical Chemistry, vol. 79, no. 9, pp. 3504-3508, 2007.

[20] K. Jiao, C. Graham, J. Wolff and P. Kohli, "Modulating molecular and nanoparticle transport in flexible polydimethylsiloxane membranes," Journal of Membrane Science, Vols. 401-402, pp. 25-32, 2012.

[21] T. Scharnweber, R. Truckenmuller, A. Schneider, A. Welle, M. Reinhardt and S. Giselbrecht, "Rapid prototyping of microstructures in polydimethylsiloxane (PDMS) by direct UV-lithography," Lab on a Chip, vol. 11, no. 7, pp. 1368-71, 2011.

[22] A. Marty, C. Causserand, C. Rogues and P. Bacchin, "Impact of tortuous flow on bacteria streamer development in microfluidic system during filtration," Biomicrofluidics, vol. 8, no. 1, 2014.

[23] D. Huh, H. Kim, J. Fraser, D. Shea, K. Mohammed, A. Bahinski, G. Hamilton and D. Ingber, "Microfabrication of human organs-on-chips," Nature Protocols, vol. 8, no. 11, pp. 2135-57, 2013.

[24] K. McCarthy and J. de Vellis, "Preparation of Separate Astroglial and Oligodendroglial Cell Cultures from Rat Cerebral Tissue," The Journal of Cell Biology, vol. 85, no. 3, pp. 890-902, 1980.

What is claimed:

1. An elastic assembly for use in a cellular assay, the assembly comprising:
   (a) a luminal compartment configured to house a first cell;
   (b) an abluminal compartment configured to house a second cell,
   (c) an elastic membrane, the elastic membrane comprising a plurality of pores therethrough and configured to separate the luminal compartment from the abluminal compartment;
   (d) an anchoring member having a window therethrough mechanically coupled to each of the elastic membrane, the luminal compartment, and the abluminal compartment; and
   (e) an actuator mechanically coupled to the anchoring member
   wherein each of elastic membrane, the luminal compartment, and the abluminal compartment are capable of elastic deformation when the physiological stress is applied to the anchoring member by the actuator.

2. The assembly of claim 1, wherein each of the luminal compartment, the abluminal compartment, and the elastic membrane comprise an elastomer.

3. The assembly of claim 2, wherein the elastomer has an elastic modulus of 1 kPa-5 MPa.

4. The assembly of claim 1, wherein the physiological stress is an acute stress or a repetitive stress.

5. The assembly of claim 4, wherein the physiological stress is associated with traumatic brain injury (TBI), a beating heart, blood flow, or hypertension.

6. The assembly of claim 1, wherein the luminal compartment is seeded with a vascular cell and/or the abluminal compartment is seeded with a neural cell; wherein the luminal compartment is seeded with a heart valve endothelial cell and/or the abluminal compartment is seeded with a heart valve interstitial cell; or wherein the luminal compartment is seeded with a nasal epithelial cell and/or the abluminal compartment is seeded with a capillary microvascular endothelial cell.

7. The assembly of claim 6, wherein the luminal compartment is seeded with an MVEC cell and the abluminal compartment is seeded with an astrocyte cell.

8. The assembly of claim 1, wherein the assembly comprises an extracellular matrix hydrogel and/or an extracellular matrix protein.

9. The assembly of claim 1, wherein the assembly is plasma activated.

10. The assembly of claim 1, wherein (i) the plurality of pores have an inter-pore spacing of less than 30 µm, (ii) each of the plurality of pores has a diameter less than 10 µm, (iii) the membrane has a thickness of no greater than 20 µm, or any combination of (i), (ii), and (iii).

11. A system for use in a cellular assay, the system comprising the assembly according to claim 1 and further comprising:
- a pump in fluid communication with the luminal compartment; and
- a detection system.

12. A kit for preparing an assembly according to claim 1, the kit comprising one or more of the elastic membrane, the luminal compartment, the abluminal compartment, the anchoring member, the first cell, the second cell, the extracellular matrix hydrogel, the extracellular protein, a media, a sealant, or any combination thereof.

13. A method for performing a cellular assay, the method comprising:
- (a) providing an assembly according to claim 1 or a system comprising the assembly of claim 1 seeded with the first cell and the second cell;
- (b) applying a stimulus to the assembly by actuating the actuator; and
- (c) detecting a characteristic of the first cell seeded into assembly, the second cell seeded into the assembly, or both.

14. The method of claim 13, wherein the stimulus is a mechanical stimulus, an electrical stimulus, a chemical stimulus, or any combination thereof.

15. The method of claim 13, wherein the stimulus is an acute stress or a repetitive stress of 1 kPa-5 MPa.

16. The method of claim 13, wherein the stimulus is an associated with a physiological stress.

17. The method of claim 16, wherein the physiological stress is associated with traumatic brain injury (TBI), a beating heart, blood flow, or hypertension.

18. The assembly of claim 1, wherein the luminal compartment has a media inlet and a media outlet and the luminal compartment is configured to have a media flow therethrough.

19. A method for modeling traumatic brain injury in a cell assay, the method comprising:
- providing an assembly according to claim 1 or a system comprising the assembly of claim 1 seeded with the first cell and the second cell,
- actuating the actuator to stretch the elastic membrane at least once by at least 10% for a duration of less than 60 ms, and
- detecting a characteristic of the first cell seeded into assembly, the second cell seeded into the assembly, or both.

20. An elastic assembly for use in a cellular assay, the assembly comprising:
- (a) a luminal compartment configured to house a first cell;
- (b) an abluminal compartment configured to house a second cell,
- (c) an elastic membrane comprising a plurality of pores therethrough;
- (d) an anchoring member having a window therethrough bonded to the elastic membrane; and
- (e) an actuator mechanically coupled to the anchoring member, wherein the anchoring member is a support layer for the elastic membrane, wherein the elastic membrane and anchoring member extend together between the luminal compartment and the abluminal compartment, and wherein the anchoring member is mechanically coupled to the elastic membrane, the luminal compartment, and the abluminal compartment such that mechanical forces applied to the anchoring member result in elastic deformation of elastic membrane, the luminal compartment, and the abluminal compartment.

* * * * *